(12) United States Patent
Cameron et al.

(10) Patent No.: US 9,642,804 B2
(45) Date of Patent: *May 9, 2017

(54) CATIONIC LIPIDS WITH VARIOUS HEAD GROUPS FOR OLIGONUCLEOTIDE DELIVERY

(71) Applicant: SIRNA THERAPEUTICS, INC., Cambridge, MA (US)

(72) Inventors: Mark Cameron, Brick, NJ (US); Jennifer R. Davis, Richboro, PA (US); Andrea R. Geiser, Lansdale, PA (US); Matthew G. Stanton, Marlton, NJ (US); Vladislav V. Telyatnikov, Willow Grove, PA (US); Lu Tian, Jamison, PA (US); Weimin Wang, Churchville, PA (US)

(73) Assignee: SIRNA THERAPEUTICS, INC., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/876,402

(22) Filed: Oct. 6, 2015

(65) Prior Publication Data

US 2016/0113874 A1    Apr. 28, 2016

Related U.S. Application Data

(63) Continuation of application No. 13/390,702, filed as application No. PCT/US2010/045854 on Aug. 18, 2010, now Pat. No. 9,181,295.

(60) Provisional application No. 61/345,754, filed on May 18, 2010, provisional application No. 61/235,476, filed on Aug. 20, 2009.

(51) Int. Cl.
| | |
|---|---|
| *A61K 9/00* | (2006.01) |
| *C07J 41/00* | (2006.01) |
| *C07J 43/00* | (2006.01) |
| *A61K 9/127* | (2006.01) |
| *A61K 31/7088* | (2006.01) |

(52) U.S. Cl.
CPC ........ *A61K 9/1272* (2013.01); *A61K 31/7088* (2013.01); *C07J 41/0055* (2013.01); *C07J 43/003* (2013.01)

(58) Field of Classification Search
CPC .... A61K 9/1272; C07J 41/0055; C07J 43/003
USPC ................................. 540/108, 113; 552/541
See application file for complete search history.

(56) References Cited

U.S. PATENT DOCUMENTS

| | | | |
|---|---|---|---|
| 6,060,455 A | 5/2000 | Fernholz et al. | |
| 2006/0083780 A1 | 4/2006 | Heyes et al. | |
| 2006/0240554 A1 | 10/2006 | Chen et al. | |
| 2008/0020058 A1 | 1/2008 | Chen et al. | |
| 2008/0188675 A1 | 8/2008 | Chen et al. | |
| 2009/0263407 A1 | 10/2009 | Dande et al. | |
| 2009/0285881 A1 | 11/2009 | Dande et al. | |

FOREIGN PATENT DOCUMENTS

| | | |
|---|---|---|
| WO | 2009086558 A1 | 7/2009 |
| WO | 2009127060 A1 | 10/2009 |
| WO | 2009132131 A1 | 10/2009 |
| WO | 2010042877 A1 | 4/2010 |
| WO | 2010054384 A1 | 5/2010 |
| WO | 2010054401 A1 | 5/2010 |
| WO | 2010054405 A1 | 5/2010 |
| WO | 2010054406 A1 | 5/2010 |

OTHER PUBLICATIONS

Guo et al., "Nonviral methods for siRNA delivery." Mol Pharm. 6(3):651-658 (2009).
Semple et al., "Rational design of cationic lipids for siRNA delivery." Nat Biotechnol. 28(2):172-176 (2010).

*Primary Examiner* — Brenda Coleman
(74) *Attorney, Agent, or Firm* — Nixon Peabody LLP; David S. Resnick

(57) ABSTRACT

The instant invention provides for novel cationic lipids that can be used in combination with other lipid components such as cholesterol and PEG-lipids to form lipid nanoparticles with siRNA, to facilitate the cellular uptake and endosomal escape, and to knockdown target mRNA both in vitro and in vivo.

17 Claims, 2 Drawing Sheets

CATIONIC LIPIDS WITH VARIOUS HEAD GROUPS FOR OLIGONUCLEOTIDE DELIVERY

CROSS-REFERENCE TO RELATED APPLICATIONS

This application is a continuation application of U.S. application Ser. No. 13/390,702 filed Feb. 16, 2012, now U.S. Pat. No. 9,181,295, issued on Nov. 10, 2015, which is a 35 U.S.C. §371 National Phase Entry Application of International Application No. PCT/US2010/045854 filed Aug. 18, 2010, which designates the U.S., and which claims benefit under 35 U.S.C. §119(e) of the U.S. Provisional Application No. 61/235,476, filed Aug. 20, 2009, and U.S. Provisional Application No. 61/345,754, filed May 18, 2010, the contents of each of which are incorporated herein by reference in their entirety

REFERENCE TO SEQUENCE LISTING SUBMITTED ELECTRONICALLY

The sequence listing of the present application is being submitted electronically via EFS-Web as an ASCII formatted sequence listing with a file name "20151006_Sequence_Listing_from_Parent_051058-081171-C", creation date of Oct. 6, 2015 and a size of 3.2 KB. This sequence listing submitted via EFS-Web is part of the specification and is herein incorporated by reference in its entirety.

BACKGROUND OF THE INVENTION

The present invention relates to novel-cationic lipids that can be used in-combination with other lipid components such as cholesterol and PEG-lipids to form lipid nanoparticles with oligonucleotides; to facilitate the cellular uptake and endosomal escape, and to knockdown target niRNA both in vitro and in vivo.

Cationic lipids and the use of cationic lipids in lipid nanoparticles for the delivery of oligonucleotides, in particular siRNA and miRNA, have been previously disclosed. Lipid nanoparticles and use of lipid nanoparticles for the delivery of oligonucleotides, in particular siRNA and miRNA, has been previously disclosed. Oligonucleotides (including siRNA and miRNA) and the synthesis of oligonucleotides has been-previously disclosed. (See U.S. patent applications: US 2006/0083780, US 2006/0240554, US 2008/0020058, US 2009/0263407 and US 2009/0285881 and PCT patent applications: WO 2009/086558, WO2009/127060, WO2009/132131, WO2010/042877, WO2010/054384, WO2010/054401, WO2010/054405 and WO2010/054406). See also Semple S. C. et al, Rational design of cationic lipids for siRNA delivery, Nature Biotechnology, published online 17 January 2010; doi:10.1038/nbt. 1602.

Butyl CLinDMA is one of the cationic lipids disclosed in US 2006/0240554. Other cationic lipids are also generically disclosed in US 2006/0240554 including Octyl CLinDMA. We have synthesized and tested both Butyl CLinDMA and Octyl CLinDMA in lipid nanoparticle formulations and found that Octyl CLinDMA has superior properies to Butyl CLinDMA. Octyl CLinDMA (otherwise known as OCD) is also described in WO2010/021865.

We adopted a rational approach to design cationic lipids for use in lipid nanoparticle formulations to deliver small interfering RNA (siRNA). Starting with the cationic lipid Octyl CLinDMA (designated, "Compound 12" in this application) as a benchmark, we designed novel cationic lipids with superior properties as-demonstrated in mouse, rat and monkey experiments.

The compounds of the instant invention contain a 1,3-diether linker.

It is an object of the instant invention to provide novel cationic lipids that can be used in combination with other lipid components such as cholesterol and PEG-lipids to form lipid nanoparticles with oligonucleotides, to facilitate the cellular uptake and endosomal escape, and to knockdown target mRNA both in vitro and in vivo.

SUMMARY OF THE INVENTION

The instant invention provides for novel cationic lipids that can be used in combination with other lipid components such as cholesterol-and PEG-lipids to form lipid nanoparticles with oligonucleotides, to facilitate the cellular uptake and endosomal escape, and to knockdown target mRNA both in vitro and in vivo.

DETAILED DESCRIPTION OF THE INVENTION

Figure 1:
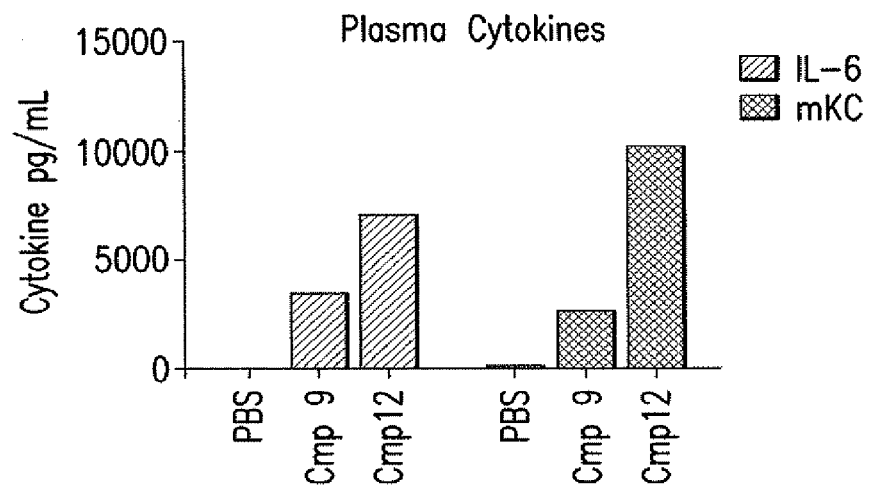
FIG. 1: Mouse in vivo Cytokine Induction 3 hour post injection.
Figure 2:
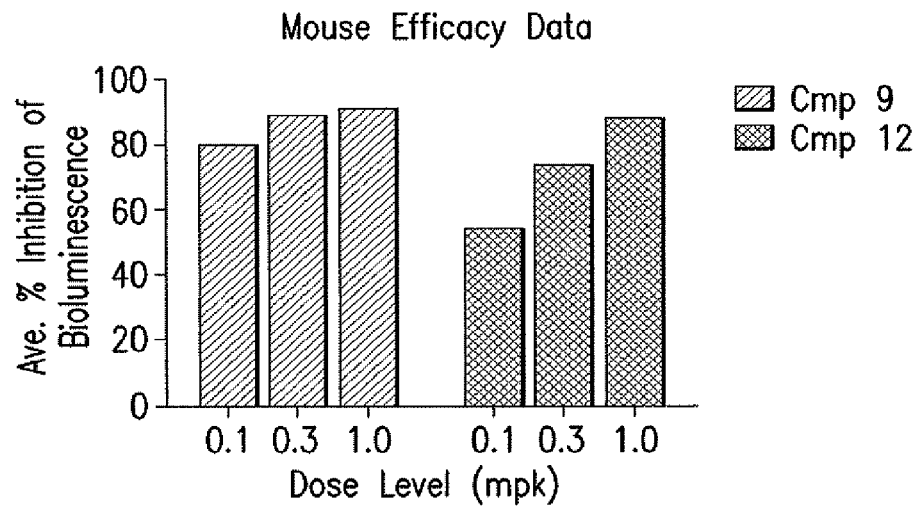
FIG. 2: Mouse data comparing Compound 12 with Compound 9.

The various aspects and embodiments of the invention are directed to the utility of novel cationic lipids useful in lipid nanoparticles to deliver oligonncleotides, in particular, siRNA and miRNA, to any target gene. (See U.S. patent applications: US 2006/0083780, US 2006/0240554, US 2008/0020058, US 2009/0263407 and US 2009/0285881 and PCT patent applications: WO 2009/086558, WO2009/127060, WO2009/132131, WO2010/042877, WO2010/054384, WO2010/054401, WO2010/054405 and WO2010/054406). See also Semple S. C. et al., Rational design of cationic lipids for siRNA delivery. Nature Biotechnology, published online 17 Jan. 2010; doi: 10.1038/nbt. 1602.

The cationic lipids of the instant invention are useful components in a lipid nanoparticle for the delivery of oligonucleotides, specifically siRNA and miRNA.

In a first embodiment of this invention, the cationic lipids are illustrated by the Formula A:

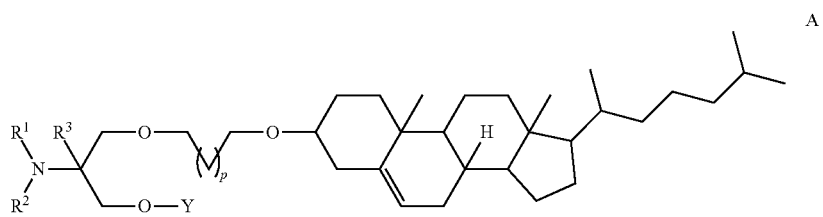

wherein:

p is 1 to 8;

$R^1$ and $R^2$ are independently selected from H, $(C_1-C_{10})$ alkyl, heterocyclyl, and a polyamine, wherein said heterocyclyl and polyamine are optionally substituted with one to three substituents selected from $R^4$, or $R^1$ and $R^2$ can be taken together with the nitrogen to which they are attached to form a monocyclic heterocycle with 4-7 members optionally containing, in addition to the nitrogen, one or two additional heteroatoms selected from N, O and S, said monocyclic heterocycle optionally substituted with one to three substituents selected from $R^4$;

$R^3$ is selected from H and $(C_1-C_6)$alkyl, said alkyl optionally substituted with one to three substituents selected from $R^4$;

$R^4$ is independently selected from halogen, $OR^5$, $SR^5$, CN, $CO_2R^5$ and $CON(R^5)_2$;

$R^5$ is independently selected from H, $(C_1-C_{10})$alkyl and aryl; and

Y is a $(C_4-C_{22})$alkyl, $(C_4-C_{22})$perfluoroalkyl, or a $(C_4-C_{22})$ alkenyl;

or any pharmaceutically acceptable salt or stereoisomer thereof.

In another embodiment, the invention features a compound having Formula A, wherein;

p is 1 to 8;

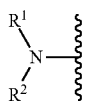

is selected from:

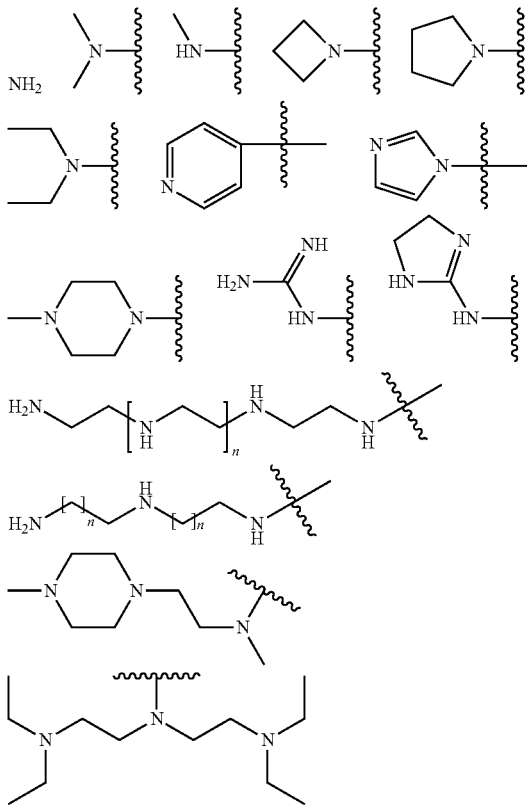

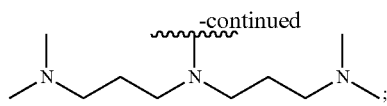

n is 1 to 10;

$R^3$ is H; and

Y is a $(C_4-C_{22})$alkyl, $(C_4-C_{22})$perfluoroalkyl, or a $(C_4-C_{22})$alkenyl;

or any pharmaceutically acceptable salt or stereoisomer thereof.

Specific cationic lipids are:

(2 S)-1-{7-[(3 β)-cholest-5-en-3-yloxy]heptyloxy}-3-[(4 Z)-dec-4-en-1-yloxy]-N,N-dimethylpropan-2-amine (Compound 4);

(2 R)-1-{4-[(3 β)-cholest-5-en-3-yloxy]butoxy}-3-[(4 Z)-dec-4-en-1-yloxy]-N,N-dimethylpropan-2-amine (Compound 5);

1-[(2 R)-1-{4-[(3 β)-cholest-5-en-3-yloxy]butoxy}-3-(octyloxy)propan-2-yl]guanidine (Compound 6);

1-[(2 R)-1-{7-[(3 β)-cholest-5-en-3-yloxy]heptyloxy}-N,N-dimethyl-3-[(9 Z, 12 Z)-octadeca-9,12-dien-1-yloxy]propan-2-amine (Compound 7);

1-[(2 R)-1-{4-[(3 β)-cholest-5-en-3-yloxy]butoxy}-N,N-dimethyl-3-[(9 Z, 12 Z)-octadeca-9,12-dien-1-yloxy]propan-2-amine (Compound 8);

(2S)-1-({6-[(3β)-cholest-5-en-3-yloxy]hexyl}oxy)-N,N-dimethyl-3-[(9Z)-octadec-9-en-1-yloxy]propan-2-amine (Compound 9);

(3β)3-[6-{[(2S)-3-[(9Z)octadec-9-en-1-yloxyl]-2-(pyrrolidin-1-yl)propyl]oxy}hexyl)oxy]cholest-5-ene (Compound 10);

(2R)-1-{4-[(3β)-cholest-5-en-3-yloxy]butoxy}-3-(octyloxy))propan-2-amine (Compound 11);

(2R)-1-({8-[(3β)cholest-5-en-3-yloxy]octyl}oxy)-N,N-dimethyl-3-(pentyloxy)propan-2-amine (Compound 13);

(2R)-1-({8-[(3β)-cholest-5-en-3-yloxy]octyl}oxy)-3(heptyloxy)-N,N-dimethylpropan-2-amine (Compound 14);

(2R)-1-({8-[(3β)-cholest-5-en-3-yloxy]octyl}oxy)-N,N-dimethyl-3-[(2Z)-pent-2-en-1-yloxy]propan-2-amine (Compound 15);

(2S)-1-butoxy-3-({8-[(3β)-cholest-5-en-3-yloxy]octyl}oxy)-N,N-dimethylpropan-2-amine (Compound 16);

(2S-1-({8-[(3β)-cholest-5-en-3-yloxy]octyl}oxy)-3-[2,2,3,3,4,4,5,5,6,6,7,7,8,8,9,9,-hexadecafluorononyl)oxy]-N,N-dimethylpropan-2-amine (Compound 17);

2-amino-3-({9-[(3β,8ξ,9ξ,14ξ,17ξ,20ξ)-cholest-5-en-3-yloxy]nonyl}oxy)-2- {[(9Z,12Z)-octadeca-9,12-dine-1-yloxy]methyl}propan-1ol (Compound 19); and;

2-amino-3-({6-[(3β,8ξ,9ξ,14ξ,17ξ,20ξ)-cholest-5en-3-yloxy]hexyl}oxy)-2-{[(9Z)-octadec-9-en-1-yloxy]methyl}propan-1-ol (Compound 20);

or any pharmaceutically acceptable salt or stereoisomer thereof.

In another embodiment, the cationic lipids disclosed are useful in the preparation of lipid nanoparticles.

In another embodiment, the cationic lipids disclosed are useful components in a lipid nonoparticle for the delivery of oligonucleotides.

In another embodiment, the cationic lipids disclosed are useful components in a lipid nanoparticle for the delivery of siRNA and miRNA.

In another embodiment, the cationic lipids disclosed are useful components in a lipid nanoparticle for the delivery of siRNA.

The following lipid nanoparticle compositions (LNPs) of the instant invention are useful for the delivery of oligonucleotides, specifically siRNA and miRNA:
Cationic Lipid/Cholesterol/PEG-DMG 56.6/38/5.4;
Cationic Lipid/Cholesterol/PEG-DMG 60/38/2;
Cationic Lipid/Cholesterol/PEG-DMG 67.3/29/3.7;
Cationic Lipid/Cholesterol/PEG-DMG 49.3/47/3.7;
Cationic Lipid/Cholesterol/PEG-DMG 50.3/44.3/5.4;
Cationic Lipid/Cholesterol/PEG-C-DMA/DSPC 40/48/2/10; and
Cationic Lipid/Cholesterol/PEG-DMG/DSPC 40/48/2/10.

The cationic lipids of the present invention may have asymmetric centers, chiral axes, and chiral planes (as described in: E. L. Eliel and S. H. Wilen, Stereochemistry of Carbon Compounds, John Wiley & Sons, New York, 1994, pages 1119-1190), and occur as racemates, racemic mixtures, and as individual diastereomers, with all possible isomers and mixtures thereof, including optical isomers, being included in the present invention. In addition, the cationic lipids disclosed herein may exist as tautomers and both tautomeric forms are intended to be encompassed by the scope of the invention, even though only one tautomeric structure is depicted.

When any variable (e.g. $R^4$) occurs more than one time in any constituent, its definition on each occurrence is independent at every other occurrence. Also, combinations of substituents and variables are permissible only if such combinations result in stable compounds.

If the ring system is bicyclic, it is intended that the bond be attached to any of the suitable atoms on either ring of the bicyclic moiety.

It is understood that substituents and substitution patterns on the cationic lipids of the instant invention can be selected by one of ordinary skill in the art to provide cationic lipids that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

It is understood that one or more Si atoms can be incorporated into the cationic lipids of the instant invention by one of ordinary skill in the art to provide cationic lipids that are chemically stable and that can be readily synthesized by techniques known in the art from readily available starting materials.

In the compounds of Formula A, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula A. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula A can be prepared without undue experimentation by conventional techniques well known to those skilled in the art or by processes analogous to those described in the Scheme and Examples herein using appropriate isotopically-enriched reagents and/or intermediates.

As used, herein, "alkyl" means a saturated aliphatic hydrocarbon having the specified number of carbon atoms.

As used herein, "alkenyl" means an unsaturated aliphatic hydrocarbon having the specified number of carbon atoms.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydro-naphthyl, indanyl and biphenyl.

As used herein, "heterocyclyl" means a 4- to 10-membered aromatic or nonaromatic heterocycle containing from 1 to 4 heteroatoms selected from the group consisting of O, N and S, and includes bicyclic groups. "Heterocyclyl" therefore includes, the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isomdolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, pipcridinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof all of which are optionally substituted with one to three substituents selected from $R^3$.

As used herein, "polyamine" means compounds having two or more primary amino groups—such as putrescine, cadaverine, spermidine, and spermine.

In an embodiment,

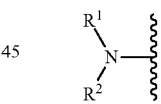

is selected from:

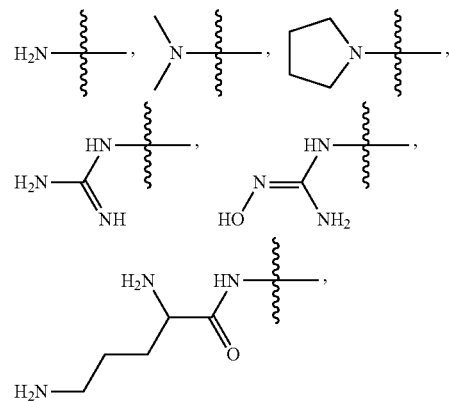

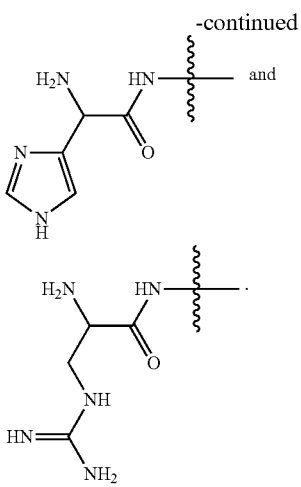

In an embodiment,

is selected from:

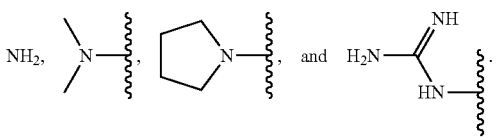

In an embodiment,

is selected from NH$_2$ and NMe$_2$.

In an embodiment,

is NH$_2$.

In an embodiment, n is 1 to 5.
In an embodiment, p is 1 to 8.
In an embodiment, R$^3$ is H or (C$_1$-C$_6$)alkyl, said alkyl is optionally substituted with from one to three OH.
In an embodiment, R$^3$ is H, methyl, ethyl or propyl, said methyl, ethyl or propyl is optionally substituted with one OH.
In an embodiment, R$^3$ is H or hydroxymethyl.
In an embodiment, R$^3$ is H.
In an embodiment, R$^4$ is independently halogen, OH, O(C$_1$-C$_6$)alkyl, SH, S(C$_1$-C$_6$)alkyl, CN, CO$_2$H, CO$_2$(C$_1$-C$_6$)alkyl, CONH$_2$, or CON(C$_1$-C$_6$)alkyl$_2$.

In an embodiment, R$^4$ is independently halogen, OH or O(C$_1$-C$_6$)alkyl.
In an embodiment, R$^5$ is independently H or (C$_1$-C$_6$)alkyl.
In an embodiment, Y is a (C$_4$-C$_{22}$)alkyl, (C$_4$-C$_{22}$)perfluoroalkyl, or a(C$_4$-C$_{22}$)alkenyl.
In an embodiment of Formula A, "heterocyclyl" is pyrolidine, piperidine, morpholine, imidazole or piperazine.
In an embodiment of Formula A, "monocyclic heterocyclyl" is pyrolidine, piperidine, morpholine, imidazole or piperazine.
In an embodiment of Formula A, "polyamine" is putrescine, cadaverine, spermidine or spermine.

Included in the instant invention is the free form of cationic lipids of Formula A, as well as the pharmaceutically acceptable salts and stereoisomers thereof. Some of the isolated specific cationic lipids exemplified herein are the protonated salts of amine cationic lipids. The term "free form" refers to the amine cationic lipids in non-salt form. The encompassed pharmaceutically acceptable salts not only include the isolated salts exemplified for the specific cationic lipids described herein, but also all the typical pharmaceutically acceptable salts of the free form of cationic lipids of Formula A. The free form of the specific salt cationic lipids described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant cationic lipids can be synthesized from the cationic lipids of this invention which contain a basic or acidic moiety by conventional chemical methods. Generally, the salts of the basic cationic lipids are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the cationic lipids of this invention include the conventional non-toxic salts of the cationic lipids of this invention as formed by reacting a basic instant cationic lipids with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic (TFA) and the like.

When the cationic lipids of the present invention are acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric; ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the cationic lipids of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

UTILITY

Cationic lipids and the use of cationic lipids in lipid nanoparticles for the delivery of oligonucleotides, in particular-siRNA and miRNA, for therapeutic purposes, have been previously disclosed. (See U.S. patent applications: US 2006/0240554 and US 2008/0020058). Lipid nanoparticles and use of lipid nanoparticles for the delivery of oligonucleotides, in particular siRNA and miRNA, for therapeutic purposes, has been previously disclosed. (See U.S. patent applications: US 2006/0240554 and US 2008/0020058). Oligonucleotides (including siRNA and miRNA) and the synthesis of oligonucleotides has been previously disclosed. (See U.S. patent applications: US 2006/0240554 and US 2008/0020058).

The utility of cationic lipids in LNPs for the delivery of oligonucleotides for therapeutic purposes is also disclosed in Guo, K. et al. Molecular Pharaceutics (2009) 6:3, 651-658; and Whitehead, K. A. et al. Nature Reviews Drug Discovery (2009) 8, 129-138.

EXAMPLES

Examples provided are intended to assist in a further understanding of the invention. Particular materials employed, species and conditions are intended to be further illustrative of the invention and not limitative of the reasonable scope thereof. The reagents utilized in synthesizing the cationic lipids are either commercially available or are readily prepared by one of ordinary skill in the art.

GENERAL SCHEMES

General Scheme 1: Synthesis of the novel cationic lipids is a convergent process whereby the Lewis acid catalyzed reaction between the epoxide (i) and the linker (ii) affords the desired alcohol regioisomer (iii). Functional group interconversion of the hydroxyl group to a suitable leaving group, for example a triflate group ((iv), X=OTf), followed by displacement with an appropriate amine affords the requisite cationic lipid (v).

General Scheme 2: Cationic lipids of type (x) can be prepared as outlined below. Aminodiols can be protected as a cyclic hemi-aminal (vi). Alkylation of the free alcohol with linoleyl mesylate can generate compounds of type (vii). Deprotection of the hemi-aminal followed by protection of the primary amine can generate alcohol (vii). Alkylation of this alcohol, deprotection of the amine and reductive animation can yield compounds of type (x).

General Scheme 3: Compounds of type (xv) can be prepared as outlined below. The amino group of tris can be protected and the diol can be converted to a cyclic ketal. Alkylation of the free alcohol can generate compound (xii). Deprotection of the ketal followed by amine reprotection can give diol (xiii). A synthetic scheme analogous to that described in General Scheme 2 would then generate compounds of type (xv).

General Scheme 4: Compounds of type (xvii) can be prepared as outlined below. 2-amino-2-(hydroxymethyl)propane-1,3-diol can be monoalkylated upon treatment with sodium hydride and a lipid electrophile in toluene to generate the mono-ether derivative (xvi). A second alkylation can be conducted under similar conditions to generate the diether tris derivatives of type (xvii).

GENERAL SCHEME 1

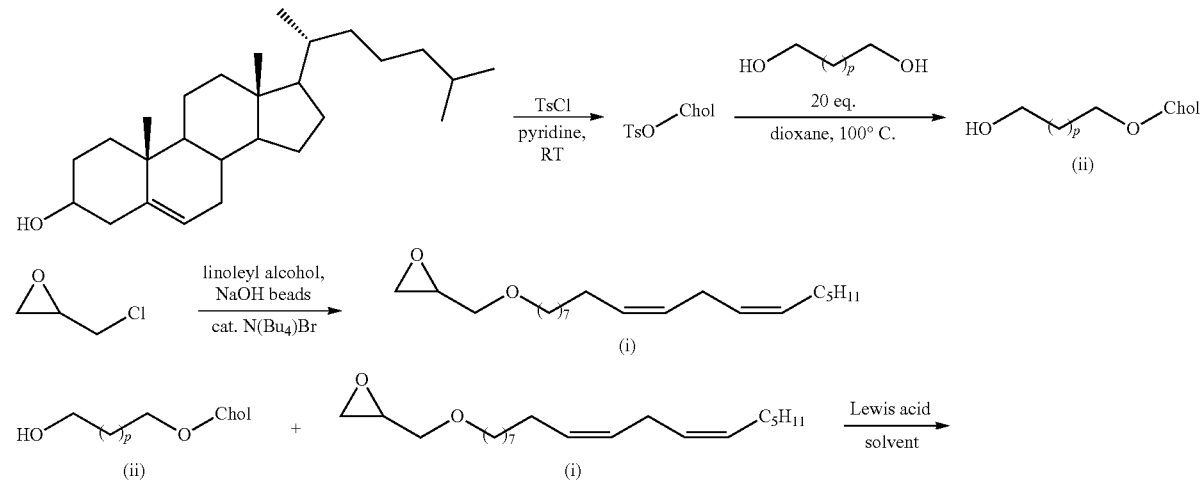

-continued
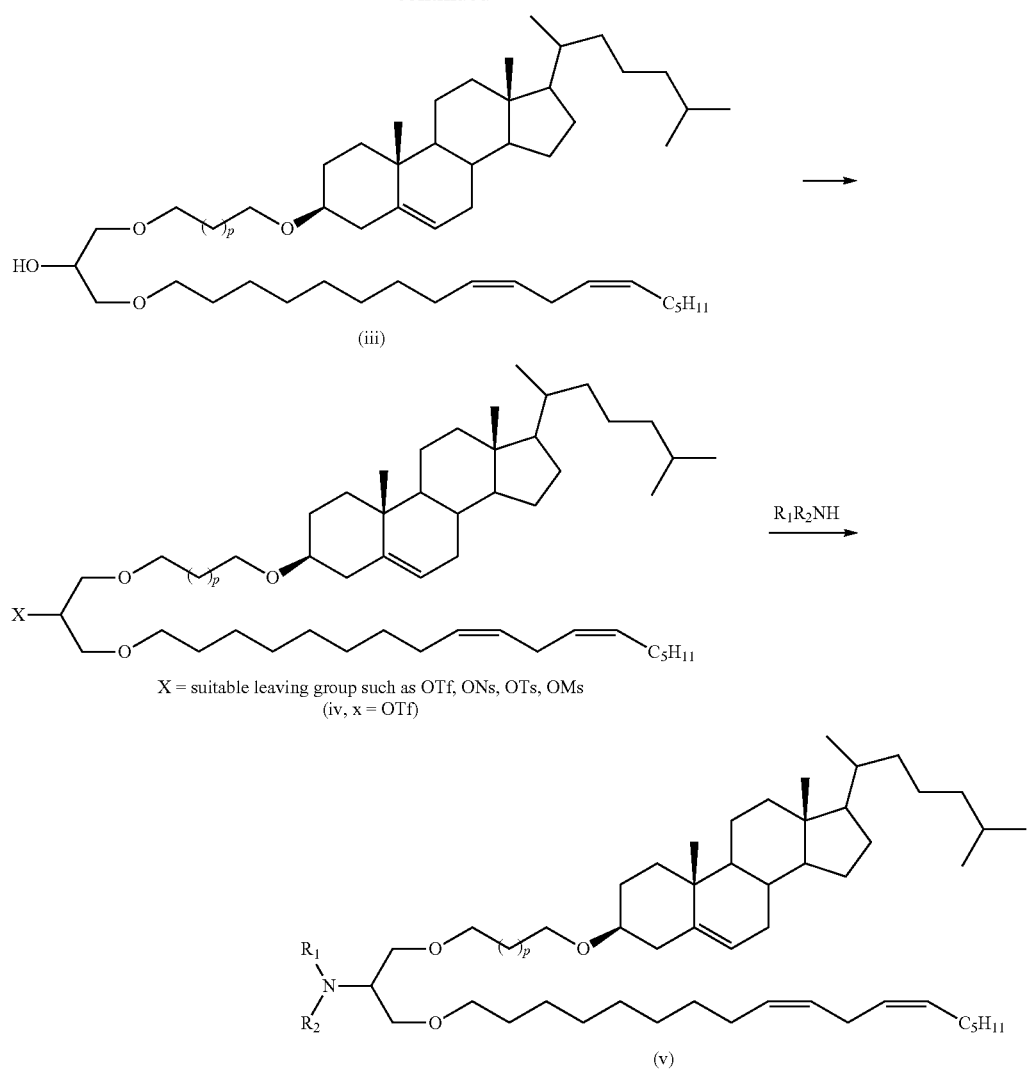
GENERAL SCHEME 2
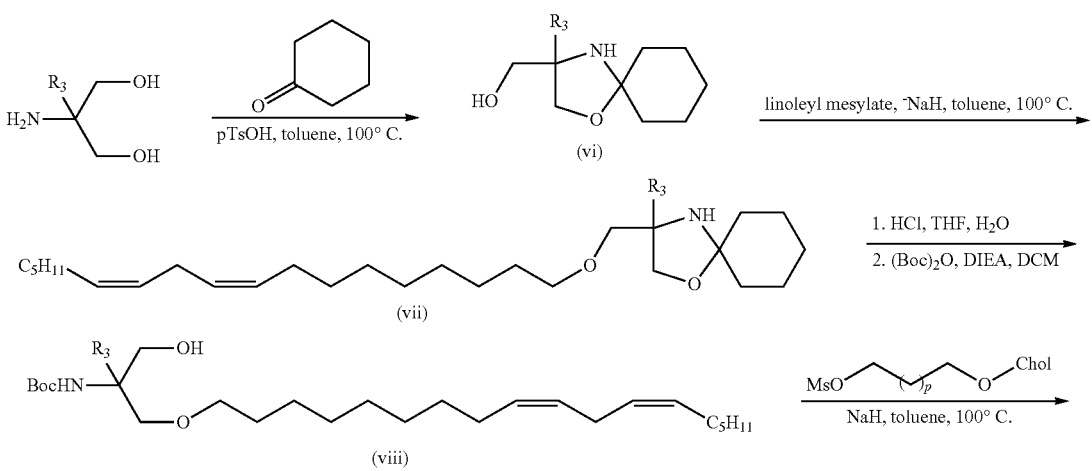

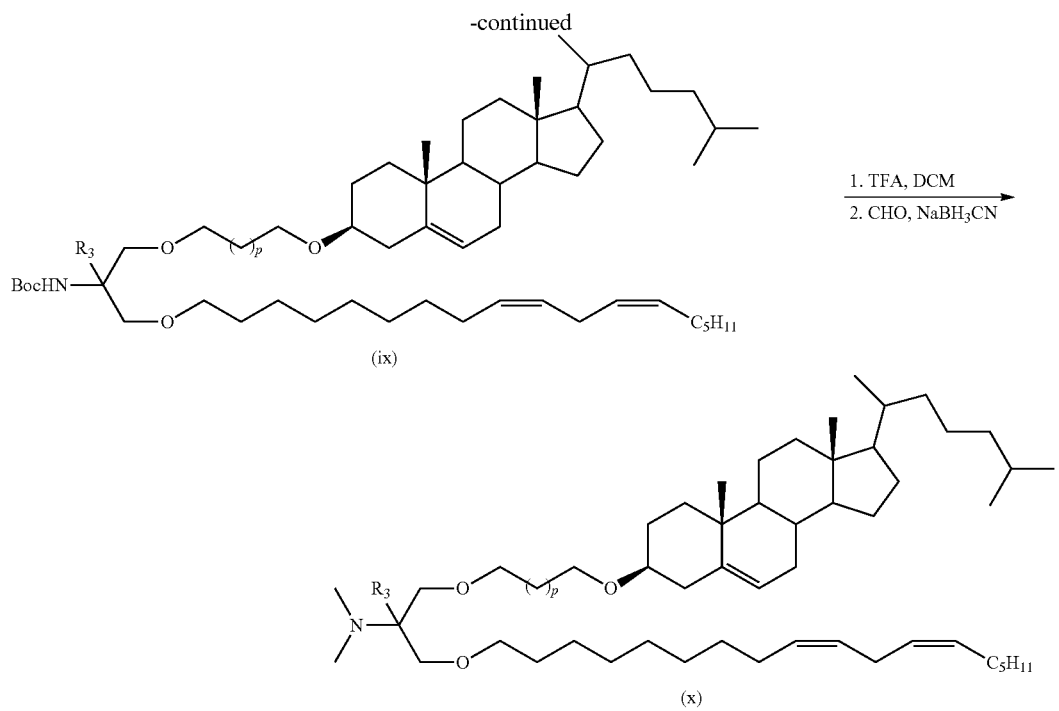
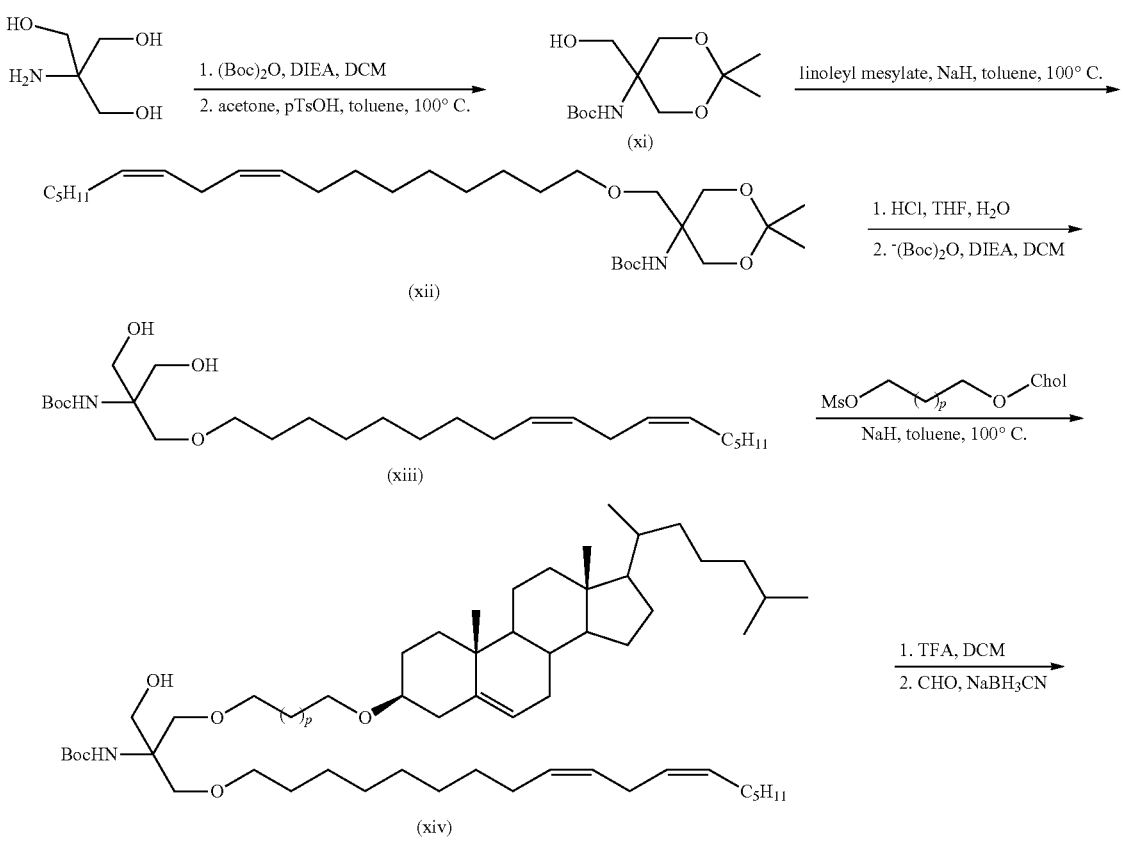
GENERAL SCHEME 3

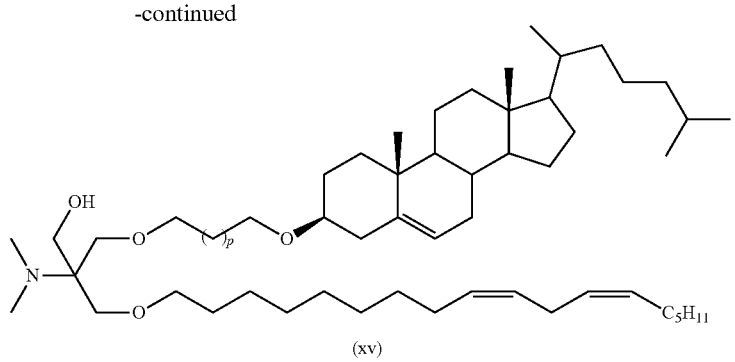

(xv)

GENERAL SCHEME 4

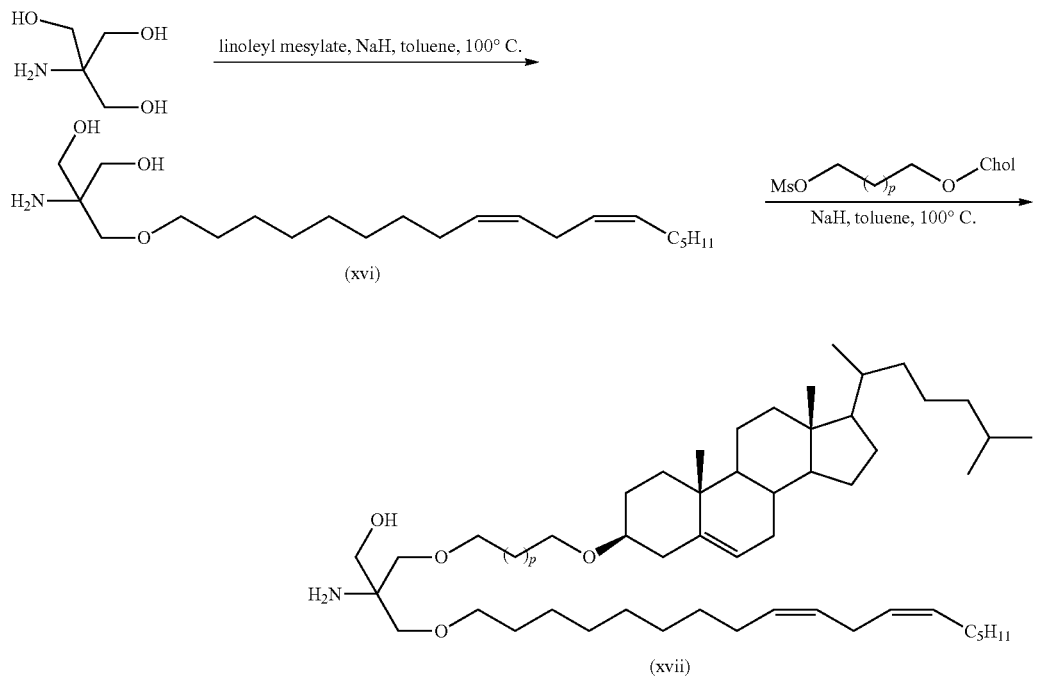

Preparation of (2R)-2-{[4Z)-dec-4-en-1-yl]methyl}oxirane (Compound 1)

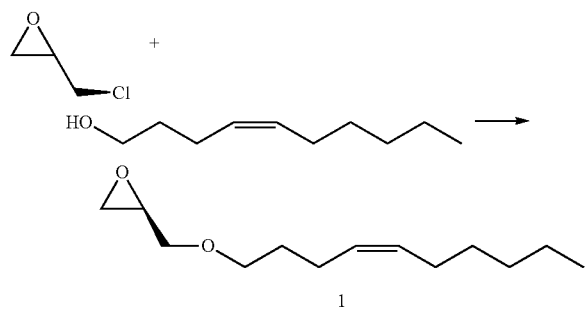

To a stirred, cooled (<5° C.) mixture of cis-4-decen-1-ol (1,14.42 g, 156 mmol), tetrabutylammonium bromide (1.26 g, 3.91 mmol) and sodium hydroxide (4.67 g, 117 mmol) was added R-(-)-epichlorohydrin (6.1 mL, 78 mmol) in one portion, the mixture was stirred for 2 hours, and then a second portion of R-(-)-epichlorohydrin (6.1 mL, 78 mmol) was added. The mixture was stirred overnight. Hexane (150 mL) was added, and the mixture filtered. The filtrate concentrated to oil, and purification through flash chromatography gave product (1, 14.3 g, 67.3 mmol) in 86% yield. Compound 1: $C_{13}H_{24}O_2$ HRMS M+H expected 213.1856; found 213.1849 amu. $^1$H NMR (500 MHz, CDCl$_3$) δ 5.34 (2H, multiplet); 3.70 (1H, dd, J=3.2, 11.5 Hz); 3.52 (1H, dt, J=6.6, 9.2 Hz); 3.47 (1H, dt, J=6.6, 9.2 Hz); 3.39 (1H, dd, J=5.5, 11.6 Hz); 3.15 (1H, multiplet); 2.80 (1H, dd, J=4.1, 4.9 Hz); 2.61, (1H, dd, J=2.7, 5.0 Hz); 2.11 (2H, q, J=7.2 Hz); 2.02 (2H, q, J=7.2 Hz); 1.66 (1H, q, J=6.7 Hz); 1.63 (1H, t, J=6.9 Hz); 1.38-1.24 (6H, complex); 0.89 (3H, t, J=6.9 Hz) ppm.

Preparation of 8-[(3β)-cholest-5-en-3-yloxy]octan-1-ol (Compound 2)

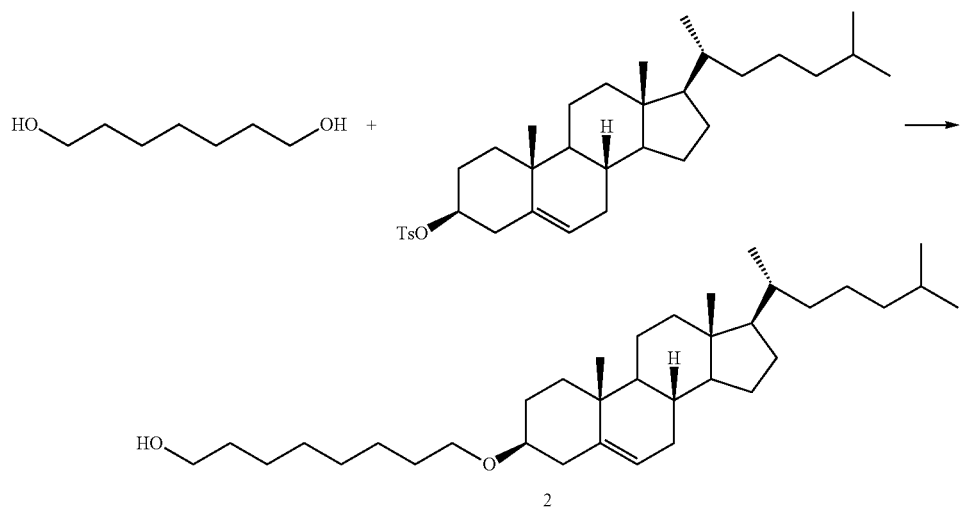

A mixture of 1,7-heptandiol (30.6 g, 231 mmol) and cholesteryl tosylate (25 g, 46.2-mmol) in toluene (80 mL) was heated at 80° C. for 16 hours. The reaction mixture was cooled to room temperature and hexane (70 mL) added. The resulting two layers were separated and the top layer collected and washed with a 1:1 solution of saturated brine and 1M $Na_2CC_3$ (100 mL), dried over $Na_2SO_4$ filtered, and finally concentrated to low volume (~40 mL). The crude oil was purified through flash chromatography to give product (2, 17.0 g, 33.9 mmol) in 73% yield. Compound 2: $C_{34}H_{60}O_2$: HRMS M+Na expected 523.4491; found 523.4486 amu. $^1$H NMR (500 MHz, $CDCl_3$) δ 5.34 (1H, complex); 3.64 (2H, complex); 3.45 (2H, complex); 3.12 (1H, complex); 2.35 (1H, ddd, J=2.2, 4.7, 13.2 Hz); 2.19 (1H, complex); 2.05-1.77 (5H, complex); 1.63-0.83 (44H, complex); 0.68 (3H,s) ppm.

Preparation of (2 R)-1-[{7-[(3 β)-cholest-5-en-3-yloxy]heptyl}oxy)-3-[(4 Z)-dec-4-en-1-yloxy]propan-2-ol. (Compound 3)

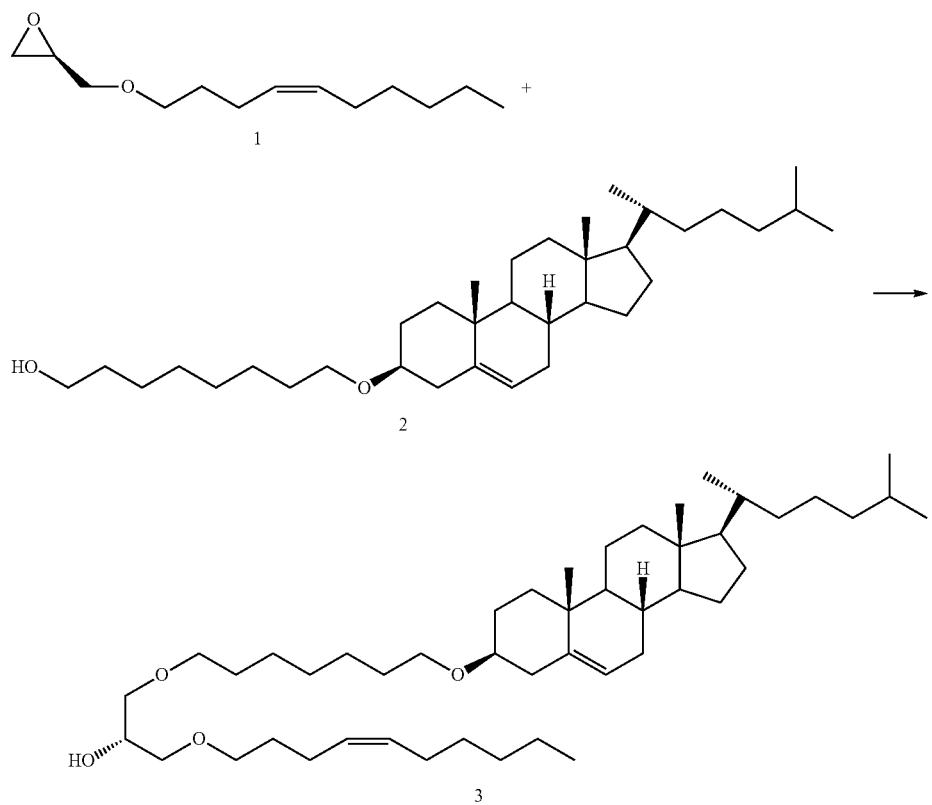

To a stirred, cooled (0° C.), solution of the alcohol (2, 6.00 g, 12 mmol) in anhydrous CH$_2$Cl$_2$ (20 mL) under an atmosphere of nitrogen was added 1M SnCl$_4$ in CH$_2$Cl$_2$ (1.2 mL, 1.2 mmol). A solution of the epoxide (1, 3.1 g, 14.6 mmol) in CH$_2$Cl$_2$ (5 mL) was added dropwise over 2 hours. The solution was stirred for a further 1 hour. The reaction was quenched with 1 M Na$_2$CO$_3$ (3 mL) and hexane (50 mL) added. The mixture was filtered, and the filtrate collected and concentrated to a crude oil (9.7 g). Purification through flash chromatography afforded product (3, 4.95 g, 6.94 mmol) in 58% yield. C$_{42}$H$_{84}$O$_4$ HRMS M+H expected 713.6442; found 713.6423 amu. $^1$H NMR (500 MHz, CDCl$_3$) δ 5.42-5.30 (3H, complex); 3.94 (1H, complex); 3.52-3.40 (10H, complex); 3.12 (1H, complex); 2.45 (1H, d, J=4.1 Hz); 2.35 (1H, ddd, J=2.4, 13.2 Hz); 2.18 (1H, br t, J=12.7 Hz); 2.09 (2H, br q, J=7.0 Hz); 2.05-1.77 (7H, complex); 1.67-0.82 (55H, complex); 0.68 (3H, s) ppm.

Preparation of (2 S )-1-{7-[(3 β)-cholest-5-en-3-yloxy]heptyloxy}-3-[(4 Z)-dec-4-en-1-yloxy]-N,N-dimethylpropan-2-amine. (Compound 4)

To a stirred cooled (0° C.) solution of the alcohol (3, 4.9g, 6.87 mmol) and anhydrous pyridine (0.7 mL, 8.67 mmol) in anhydrous CH$_2$Cl$_2$ (20 mL), under a nitrogen atmosphere, was added triflic anhydride (1.4 mL, 8.3 mmol) dropwise. The solution was stirred for 2 hours, and then added to a 2M solution of dimethylamine in THF (18 mL, 36 mmol) at 0° C. The solution was stirred for 2 hours, and then dichloromethane (150 mL) added. The solution was then washed with 0.5 M NaHCO$_3$ (150 mL). The organic layer was separated and dried over sodium sulfate, filtered and concentrated to oil (6.2 g). Hexane (60 mL) was added, the solids formed removed by filtration and the filtrate concentrated to give a crude oil (5.4 g). Purification through chromatography afforded product (4, 2.83 g, 3.82 mmol) in 56% yield. C$_{49}$H$_{87}$NO$_3$ HRMS M+H expected 740.6921; found 740.6898 amu. $^1$H NMR (500 MHz, CDCl$_3$) δ 5.41-5.31 (3H, complex); 3.53 (2H, dd, J=5.6, 9.9 Hz); 3.47 (2H, dd, J=5.6, 9.9 Hz); 3.44 (2H, multiplet); 3.41 (2H, t, J=6.9 Hz); 3.40 (2H, t, J=6.9 Hz); 3.12 (1H, multiplex); 2.73 (1H, multiplet); 2.38 (6H,s); 2.35 (1H, ddd, J=2.2, 4.8, 13.1 Hz); 0.84-2.25 (64 H, complex); 0.68 (3H, s) ppm.

Compounds 5-11 and 13-17 are novel cationic lipids. Compound 12 is S-Octyl CLinDMA. The Compounds can be prepared according to the Scheme above. The synthesis of Compound 9 is shown below.

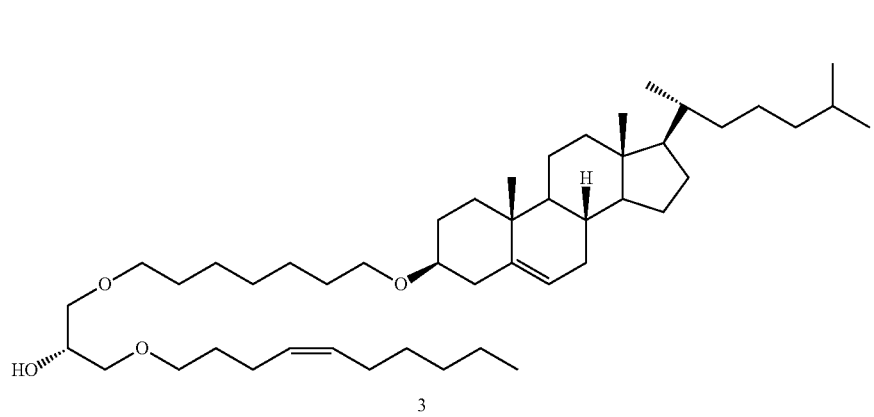

3

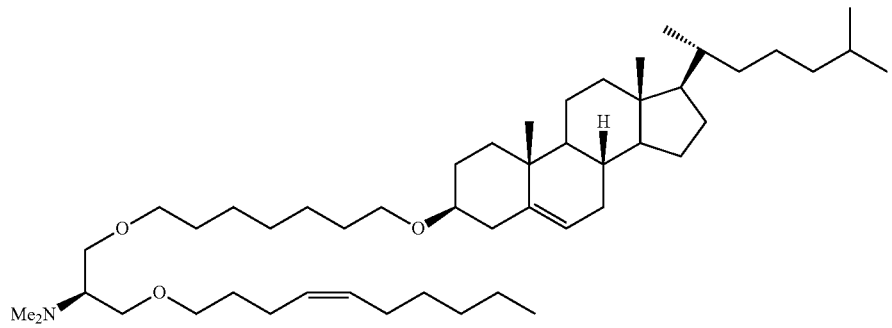

4

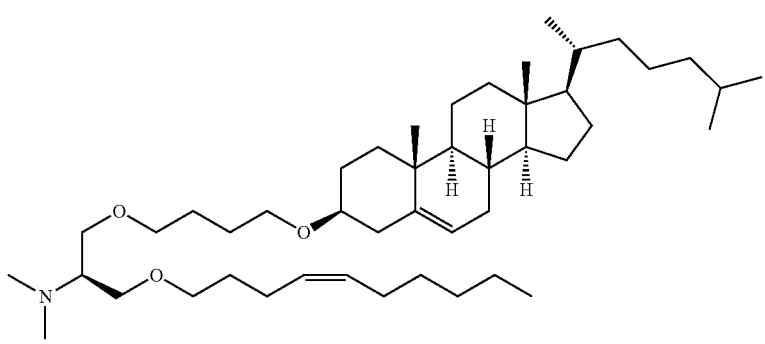
Compound 5
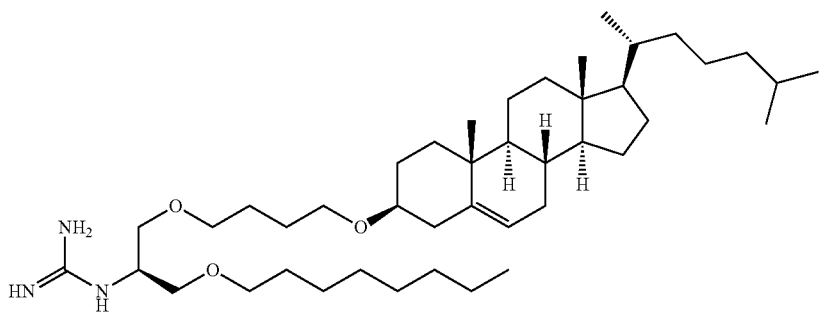
Compound 6
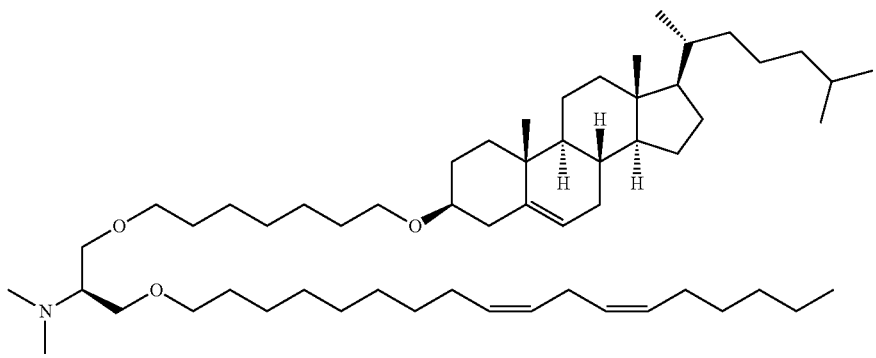
Compound 7
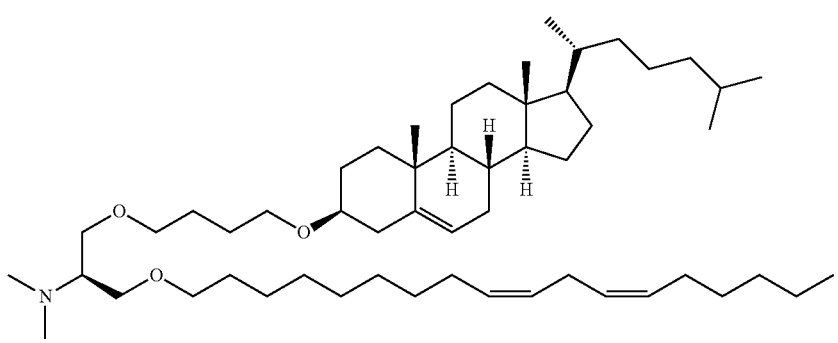
Compound 8

-continued
Compound 9
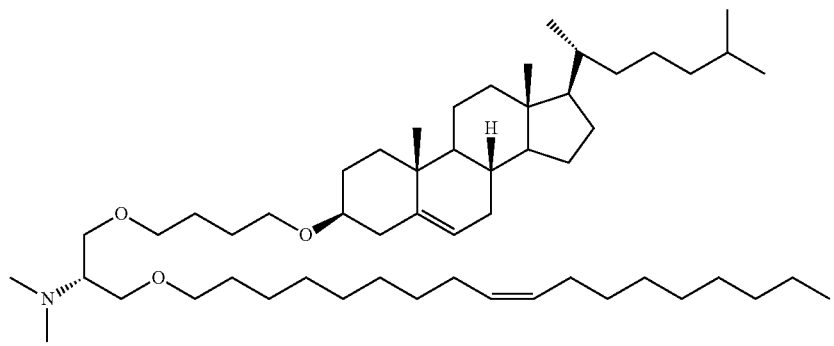
Compound 10
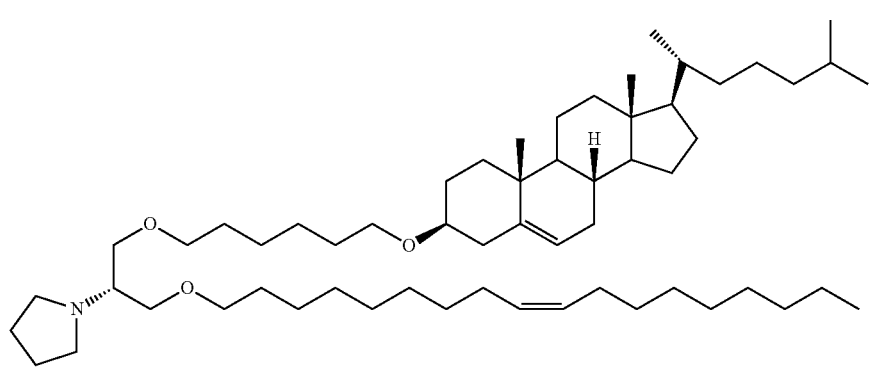
Compound 11
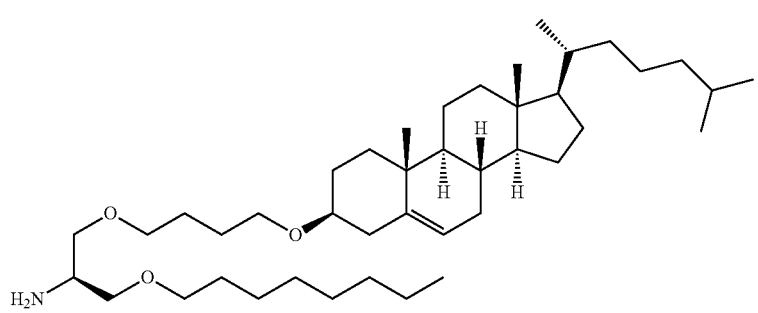
Compound 12
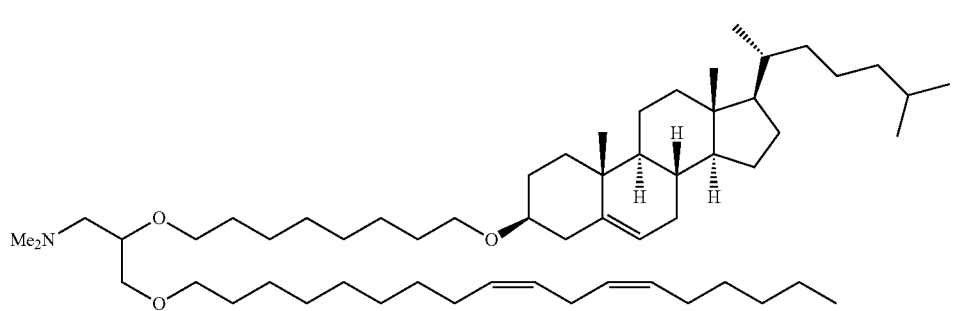
Compound 13
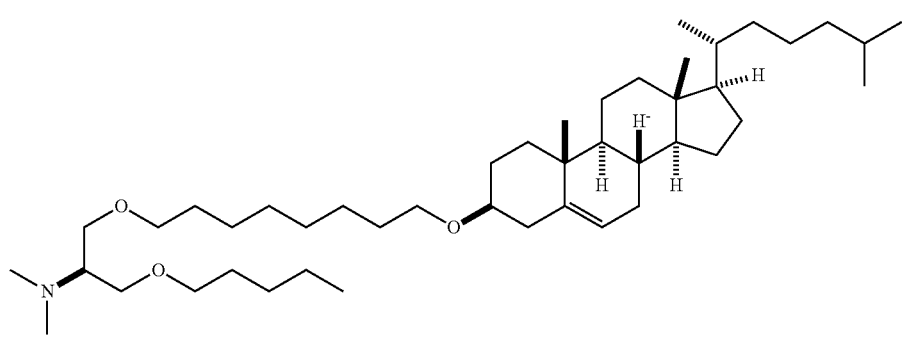

-continued
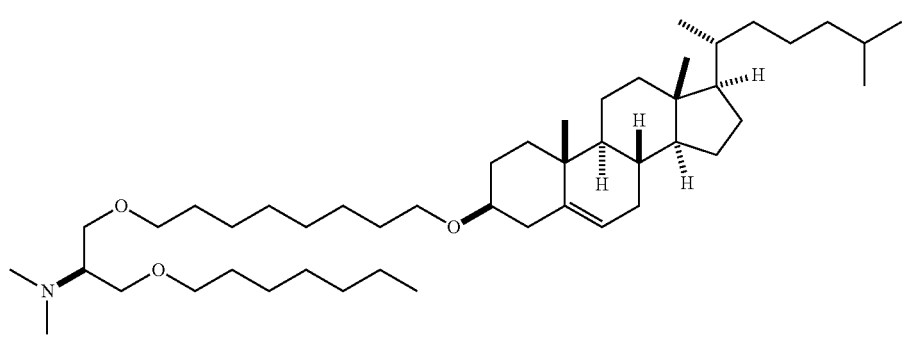
Compound 14
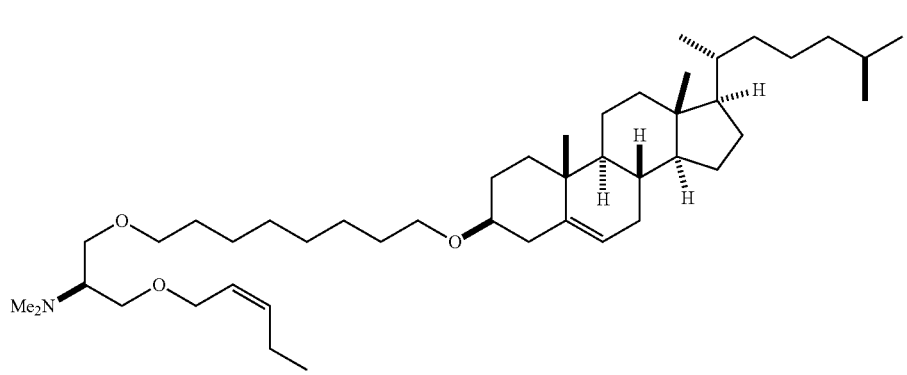
Compound 15
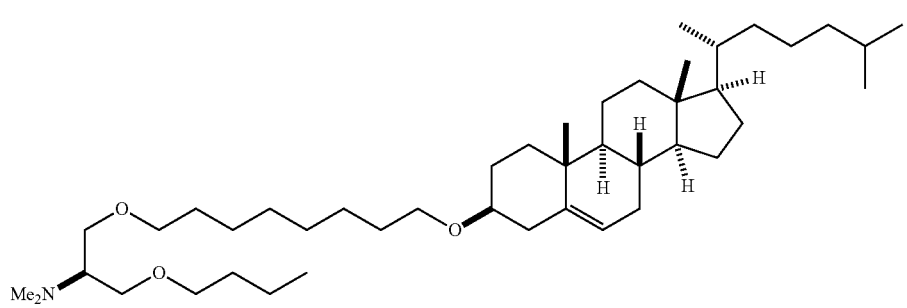
Compound 16
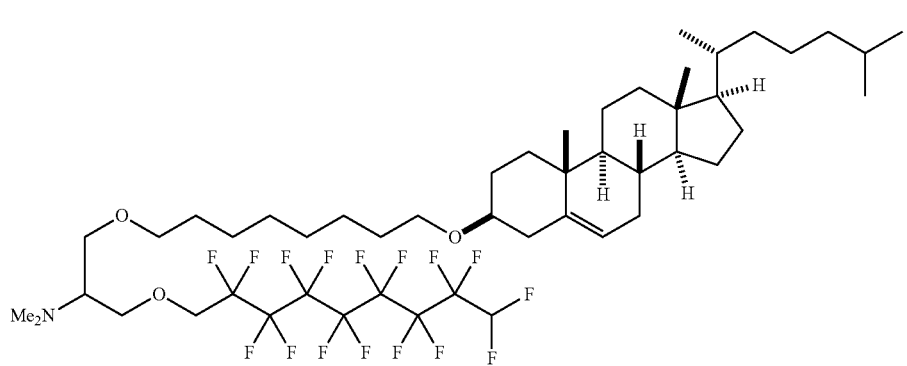
Compound 17

Preparation of (2S)-1-({6-[(3β)-cholest-5-en-3-yloxylhexyl}oxy)-N,N-dimethyl-3-[(9 Z)-octadec-9-en-1-yloxylpropan-2-amine. (Compound 9)

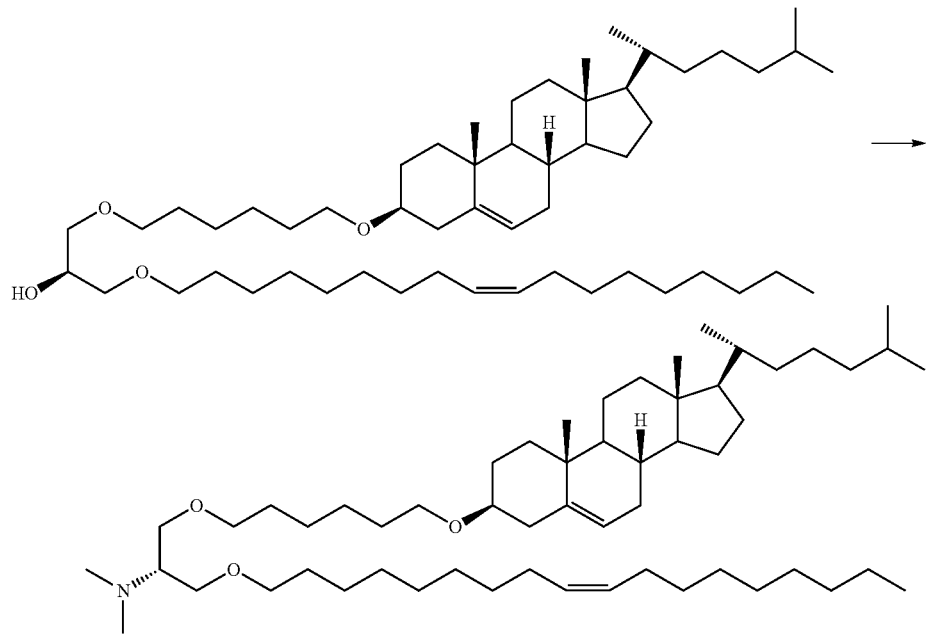

9

To a stirred, chilled (−7° C.) solution of the alcohol (41.99 g, 50.3 mmol) and lutidine (5.90 g, 55.1 mmol) in anhydrous CH$_2$Cl$_2$ (420 mL) was added triflic anhydride (9 mL, 53.3 mmol) portion wise over 30 minutes. The solution was stirred for 2.5 hours, and then transferred to a stirred cooled (2° C.) 2M NHMe$_2$ in THF (1425 mL, 2850 mmol). The solution was then stirred for 3 hours. Evaporated volatiles and dissolved oily residue in hexanes (500 mL) and washed with 10% Na$_2$CO$_3$ (500 mL). The phases separated and aqueous phase back extracted with hexanes (200 mL). The organic phases were combined and washed with water (200 mL), and dried organic over Na$_2$SO$_4$. The solution filtered and evaporate volatiles and purified crude through HPFC to afford compound 9 (25.5 g, 30.4 mmol) in 60% yield. C$_{56}$H$_{103}$NO$_3$ HRMS (ESI positive) M+H, theory m/z 838.8017 amu, measured m/z 838.7996 amu. $^1$H NMR (400 MHz, CDCl$_3$) δ 5.36-5.33 (3H, complex); 4.13-3.40 (10H, complex); 3.13 (1H, multiplet); 2.76 (1H, multiplet); 2.40 (6H, s) 2.35, (1H, ddd, J=2.3, 4.8, 13.2 Hz); 2.18 (1H, complex); 2.06-0.86 (77H, complex); 0.68 (3H,s) ppm.

Compound 5: (2 R )-1-{4-[(3 β)-cholest-5-en-3-yloxy]butoxy}-3-[(4 Z)-dec-4-en-1-yloxy]- N,N-dimethylpropan-2-amine.

2.70 g, 3.90 mmol, 57% yield. C$_{46}$H$_{83}$NO$_3$: HRMS (ESI positive) M+H, theory m/z 698.6446, measured m/z 698.6480. $^1$H NMR (500 MHz, CDCl$_3$) δ 5.42-5.31, (3H, complex); 3.57-3.38, (10H, complex); 3.12 (1H, multiplet); 2.73, (1H, multiplet); 2.38 (6H, s); 2.35, (1H, ddd, J=2.3, 4.8, 13.2 Hz); 2.22-0.84 (58H, complex); 0.68, (3H, s) ppm.

Compound 6: 1-[(2 R)-1-{4-[(3 β)-cholest-5-en-3-yloxy]butoxy}-3-(octyloxy)propan-2-yl]guanidine 1.28 g, 1.87 mmol, 51% yield, C$_{43}$H$_{79}$N$_3$O$_3$: HRMS (ESI positive) M+H, theory m/z 686.6194 amu, measured m/z 686.6201 amu. $^1$H NMR (500 MHz, CDCl$_3$) δ 7.92 (1H, d, J=5.9 Hz); 7.52 (2H, br); 7.13 (2H, br); 5.34 (1H, complex); 3.71-3.40 (10H, complex); 3.12 (1H, complex); (2.35 (1H, ddd, 2.2, 4.6, 13.4 Hz); 2.18 (1H, complex); 2.03-0.82 (57H); 0.68 (3H,s) ppm.

Compound 7: 1-[(2 R )-1-{7-[(3 β)-cholest-5-en-3-yloxy]heptyloxy}-N,N-dimethyl-3-[(9 Z, 12 Z)-octadeca-9,12-dien-1-yloxy]propan-2-amine.

2.00 g, 2.35 mmol, 64% yield. C$_{57}$H$_{103}$N$_3$: HRMS (ESI positive) M+H, theory m/z 850.8011 amu, measured m/z 850.8011 amu. $^1$H NMR (500 MHz, CDCl$_3$) δ 5.42-5.29 (5H, complex); 3.53 (2H, dd, J=5.6, 9.9 Hz); 3.47 (2H, dd, J=5.6, 9.9 Hz); 3.44 (2H, multiplet); 3.40 (2H, t, 6.6 Hz); 3.39 (2H, t, 6.6 Hz); 3.12 (1H, multiplet); 2.77 (2H, t, 6.7 Hz); 2.71 (1H, multiplet); 2.37 (6H, s); 2.35 (1H, ddd, J=2.3, 4.6, 13.2 Hz); 2.18 (1H, multiplet); 2.08-1.93 (6H, complex); 1.92-1.78 (3H, complex); 1.70-0.84 (66H, complex); 0.68 (3H, s) ppm.

Compound 8: 1-[(2 R )-1-{4-[(3 β)-cholest-5-en-3-yloxy]butoxy}-N,N-dimethyl-3-[(9 Z, 12 Z)-octadeca-9,12-dien-1-yloxy]propan-2-amine.

2.90 g, 3.60 mmol, 56% yield. C$_{54}$H$_{97}$NO$_3$: HRMS (ESI positive) M+H, theory m/z 808.7654 amu, measured m/z 808.7580 amu. $^1$H NMR (500 MHz, CDCl$_3$) δ 5.42-5.30 (3H complex); 3.56-3.37 (10H, complex); 3.12 (1H, complex); 2.77 (2H, t, J=6.5 Hz); 2.72 (1H, multiplet); 2.38 (6H,s); 2.35 (1H, ddd, J=2.3, 4.5, 13.4 Hz); 2.26-0.83 (70H, complex); 0.68 (3H,s) ppm.

Compound 9: (2S)-1-({6-[(3β))-cholest-5-en-3-yloxy]hexyl}oxy)-N,N-dimethyl-3-[(9 Z)-octadec-9-en-1-yloxy]propan-2-amine.

14.2 g, 16.9 mmol. 68% yield. $C_{56}H_{103}NO_3$ HRMS (ESI positive) M+H, theory m/z 838.8017 amu, measured m/z 838.7996 amu. $^1$H NMR (400 MHz, CDCl$_3$) δ 5.36-5.33 (3H, complex); 4.13-3.40 (10H, complex); 3.13 (1H, multiplet); 2.76 (1H, multiplet); 2.40 (6H, s) 2.35, (1H, ddd, J=2.3, 4.8, 13.2 Hz); 2.18 (1H, complex); 2.06-0.86 (77H, complex); 0.68 (3H,s) ppm.

Compound 10: (3β)-3-[6-{[(2S)-3-[(9Z)-octadec-9-en-1-yloxyl]-2-(pyrrolidin-1-yl)propyl]oxy}hexyl)oxy]cholest-5-ene.

1.72 g, 1.99 mmol,81% yield $C_{58}H_{105}NO_4$ HRMS (ESI positive) M+H, theory m/z 864.8172 amu, measured m/z 864. 8240 amu. $^1$H NMR (500 MHz, CDCl$_3$) δ 5.38-5.30 (3H, complex); 3.58-3.52 (4H, complex); 3.48-3.39 (6H, complex); 3.12 (1H, multiplet); 2.66 (4H, br); 2.50 (1H, q, J=4 Hz); 2.36 (1H, ddd, J=2, 4, 12 Hz) 2.18 (1H, multiplet) 2.05-1.75 (14H, complex); 1.57-0.86 (66H, complex); 0.68 (3H,s) ppm.

Compound 11: (2R)-1-{4-[(3β)-cholest-5-3-yloxy]butoxy}-3-(octyloxy)propan-2-amine.

3.79 g. 5.88 mmol, 76% yield. $C_{42}H_{77}NO_{43}$ HRMS (ESI positive) M+H, theory m/z 644.5976 amu, measured m/z 644.6012 amu. $^1$H NMR(400 MHz, CDCl$_3$) δ 5.73 (2H, br); 5.29 (1H, multiplet); 3.56-3.35 (10H, complex); 3.08 (1H, multiplet); 2.29 (1H, multiplet); 2.13 (1H, multiplet); 2.01-1.74 (4H, complex); 1.64-0.81 (54H, complex); 0.64 (3H, s) ppm.

Compound 13: (2R)-1-({8-[(3β)-cholest-5-en-3-yloxy]octyl}oxy)-N,N-dimethyl-3-(pentyloxy)propan-2-amine.

$C_{45}H_{83}NO_3$ HRMS (ESI positive) M+H, theory m/z 686.6446 amu, measured m/z 686.6443 amu. $^1$H NMR (400 MHz, CDCl$_3$) δ 5.30 (1H, multiplet); 3.50-3.33 (10H, complex); 3.06 (1H, multiplet); 2.66 (1H, multiplet); 2.31 (6H, singlet); 2.29 (1H, multiplet); 2.13 (1H, multiplet); 1.94-1.72 (5H, complex); 1.53-0.80 (54H, complex); 0.62 (3H, singlet) ppm.

Compound 14: (2R)-1-({8-[(3β)-cholest-5-en-3-yloxy]octyl}oxy)-3-(heptyloxy)-N,N-dimethylpropan-2-amine.

$C_{47}H_{87}NO_3$ HRMS (ESI positive) M+H, theory m/z 714.6759 amu, measured m/z 714.6746 amu. $^1$H NMR (400 MHz, CDCl$_3$) δ 5.30 (1H, multiplet); 3.52-3.35 (10H, complex); 3.08 (1H, multiplet); 2.67 (1H, multiplet); 2.33 (6H, singlet); 2.30 (1H, multiplet); 2.15 (1H, multiplet); 2.00-1.74 (5H, complex); 1.59-0.82 (58H, complex); 0.64 (3H, singlet) ppm.

Compound 15: (2R)-1-({8-[(3β)-cholest-5-3-yloxy]octyl}oxy)-N,N-dimethyl-3-[(2Z)-pent-2-en-1-yloxy]propan-2-amine.

$C_{45}H_{81}NO_3$ HRMS (ESI positive) M+H, theory m/z 684.6289 amu, measured m/z 684.6276 amu. $^1$H NMR (400 MHz, CDCl$_3$) δ 5.49 (2H, multiplet); 5.30 (1H, multiplet); 3.99 (2H, d, J=6 Hz); 3.51-3.33 (8H, complex); 3.08 (1H, multiplet); 2.69 (1H, multiplet); 2.33 (6H, singlet); 2.30 (1H, multiplet); 2.20-1.70 (8H, complex); 1.51-0.82 (48H, complex); 0.64 (3H, singlet) ppm.

Compound 16: (2S)-1-butoxy-3-({8-[(3β)-cholest-5-en-3-yloxy]octyl}oxy)-N,N-dimethylpropan-2-amine.

$C_{44}H_{81}NO_3$ HRMS (ESI positive) M+H, theory m/z 672.6289 amu, measured m/z 672.6285 amu. $^1$H NMR (400 MHz, CDCl$_3$) δ 5.31 (1H, multiplet); 3.51-3.34 (10H, complex); 3.08 (1H, multiplet); 2.67 (1H, multiplet); 2.33 (6H, singlet); 2.30 (1H, multiplet); 2.14 (1H, multiplet); 2.00-1.75 (5H, complex); 1.54-0.81 (52H, complex); 0.64 (3H, singlet) ppm.

Compound 17: (2S-1-({8-[(3β)-cholest-5-en-3-yloxy]octyl}oxy-3-[2,2,3,3,4,4.5,5,6,6,7,7,8.8.9,9-hexadecafluorononyl)oxyl]N,N-dimethylpropan-2-amine.

$C_{49}H_{75}F_{16}NO_3$ HRMS(ESI positive) M+H, theory m/z 1030.5564 amu, measured m/z 1030.5506 amu. $^1$H NMR (500 MHz, CDCl$_3$) δ 6.15-5.89 (1H, tt, J=6.3, 65.0 Hz); 5.30 (1 H, multiplet); 3.95-3.88 (2H, t, J=16.8 Hz); 3.69 (2H, multiplet); 3.51-3.33 (6H, complex); 3.08 (1H, multiplet); 2.72 (1H, multiplet); 2.33 (6H, singlet); 2.03 (1H, multiplet); 2.15 (1H, multiplet); 1.96 (2H, multiplet); 1.80 (3H, multiplet); 1.56-0.82 (45H, complex); 0.64 (3H, singlet) ppm.

$^{19}$FNMR (500 MHz, CDCl$_3$) δ–119.92 (2F, singlet); –122.40 (6F, singlet); –123.73 (4F, singlet); –129.74 (2F, singlet); –137.33 to –137.44 (2F, doublet, J=55.0 Hz) ppm.

Preparation of 2-amino-2-{[(9Z,12Z)-octadeca-9,12-dien-1-yloxy]methyl}propane-1,3-diol. (Compound 18)

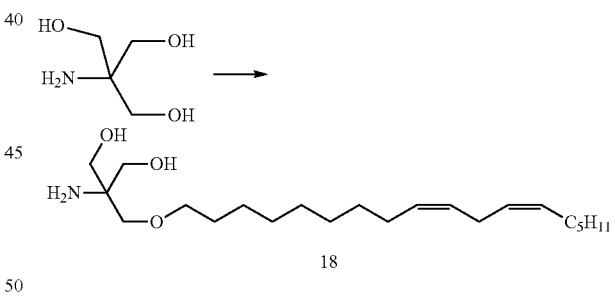

18

To a stirred solution of sodium hydride (2.2 g, 55 mmol) in toluene (200 ml) at 0° C. was added 2-amino-2-(hydroxymethyl)propane-1,3-diol (5 g, 41.3 mmol) slowly. The resulting slurry was stirred at 0° C. for 1 hour. To this mixture was added linoleyl mesylate (15 g, 43.5 mmol) and the resulting mixture was stirred for 18 hours at ambient temperature. The reaction was quenched by slow addition of isopropyl alcohol followed by ice. The reaction was partitioned between ether and water. The organics were washed with water and brine, dried over magnesium sulfate; filtered and evaporated in vacuo. The title compound was purified by flash chromatography (0-20% MeOH/DCM-ammonia) to give 3.25 g of desired product. $^1$H NMR (400 MHz, CDCl$_3$) δ 5.39 (m, 4H), 3.53 (s, 4H), 3.49 (s, 2H), 3.43 (t, J=6.59 Hz, 2H), 3.41 (s, 2H), 2.78 (t,J=6.4 Hz, 2H), 2.05 (m, 6H), 1.72 (bs, 4H), 1.57 (m, 4H), 1.34 (m, 14H),0.89 (t, J=6.78 Hz, 3H).

Preparation of 2-amino-3-({9-[(3β,8ξ,9ξ,14ξ,17ξ, 20ξ)-cholest-5en-3-yloxy]nonyl}oxy)-2-{[(9Z, 12Z)-octadeca-9,12-dien-1-yloxy]methyl}propan-1-ol. (Compound 19)

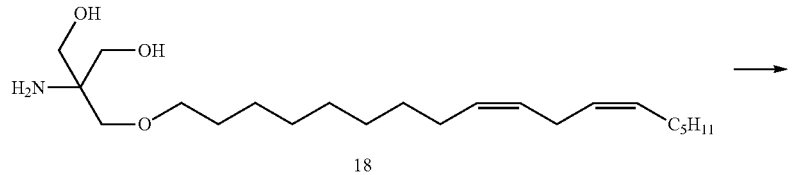
18

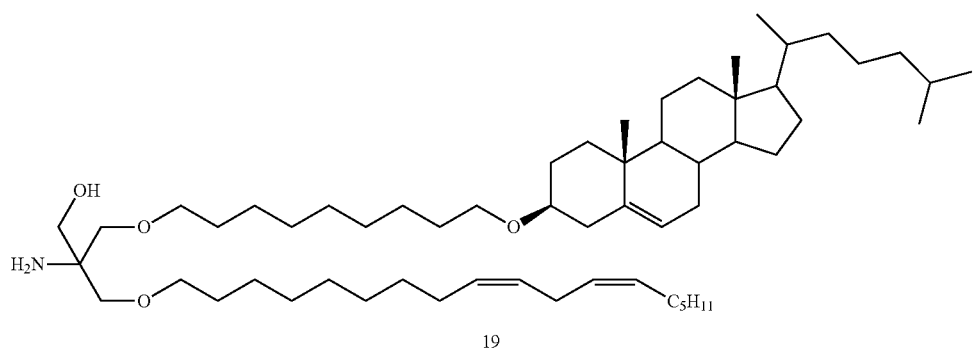
19

To a stirred solution of of 2-amino-2-{[(9Z,12Z)-octadeca-9,12-dien-1-yloxy]methyl}propane-1,3-diol (2.7 g, 7.31 mmol) in toluene (50 mL) at 0° C. was added sodium hydride (0.44 g, 11 mmol) in small portions. The resulting slurry was aged for 30 minutes and treated with 9-[(3β,8ξ, 9ξ,14ξ,17ξ,20ξ)-cholest-5-en-3-yloxy]nonyl methanesulfonate (6.5 g, 11 mmol). The reaction was heated to reflux for 24 hours, then cooled to 0° C. and quenched with water. The reaction was partitioned between water/ethyl acetate and the organics were washed with water and brine, dried over sodium sulfate, filtered and evaporated in vacuo. The crude material was purified by flash chromatography (0-10% EtOH/EtOAc) to provide 0.91 g (14%) of title compound as a colorless oil. $^1$H NMR (400 MHz, CDCl$_3$) δ 5.36 (m, 4H), 3.50 (bd, 2H, 3.42 (m, 8H), 3.15 (m, 1H), 2.85 (m, 1H)( 2.77 (t, J=6.59 Hz, 2H), 2.38 (m, 1H), 2.18 (m, 1H), 2.10-1.80 (complex, 10H), 1.60-0.80 (complex, 67H), 0.68 (s, 3H); HRMS (ESI positive) M+H, theory m/z 866.7960 amu, measured m/z 866.7981 amu.

Preparation of 2-amino-3-({6-[(3β,8ξ,9ξ,14ξ,17ξ, 20ξ)-cholest-5-en-3-yloxy]hexyl}oxy)-2-{[9Z)-octadec-9-en-1-yloxy]methyl}propan-1ol. (Compound 20)

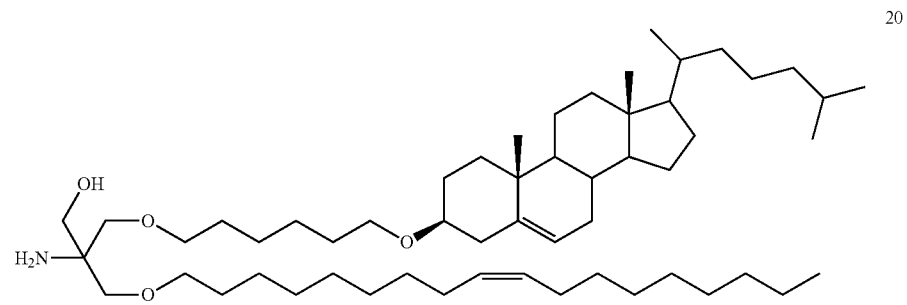 [SMILES: CCCCCCCC/C=C\CCCCCCCCOCC(N)(CO)COCCCCCCO[C@H]1CC[C@@]2(C)C(=CCC3C4CCC(C(C)CCCC(C)C)[C@@]4(C)CCC32)C1]
20

Compound 20 was prepared according to general Scheme 4 as described for compound 19. HRMS (ESI positive) M+H, theory m/z 840.7803 amu, measured m/z 840.7808 amu. ¹H NMR (400 MHz, CDCl₃) δ 5.37 (m, 2H), 3.42 (m, 10H), 3.12 (m, 1H), 2.83 (bs. 1H), 2.35 (m, 1H), 2.18 (m, 1H), 2.05-1.78 (complex, 10H), 1.55-0.85 (complex, 69H), 0.68 (s, 3H).

ADDITIONAL INFORMATION

General Scheme 1, described above, depicts the reaction of linoleyl alkoxide, formed under the conditions stated, and epichlorohydrin. Our original understanding of this reaction was that it occurred via a SN2 mechanism at the carbon bearing the halide atom with no change at the asymmetric carbon centre, for example, as depicted in the synthesis of Compound 1. Subsequent chemical modifications of Compound 1, as depicted, lead to Compound 4 with the stereochemistry unchanged at that position.

However, recent studies (experiments on the reaction of lineolyl alcohol with S-epichlorohydrin, under conditions described, Lewis acid conditions and in conjunction with vibrational circular dichroism (VCD) experiments, a valid spectroscopic method for determining absolute configuration of chiral molecules (R. K. Dukor and L. A. Nafie, in *Encyclopedia of Analytical Chemistry: Instrumentation and Applications*, Ed. R. A. Meyers (Wiley, Chichester, 2000) 662-676.)), have revealed the reaction to occur via a SN2' mechanism ie reaction at the terminal carbon of the epoxide leading to subsequent ring opening, followed by an in situ ring closing step that leads to inversion of stereochemistry at the asymmetric carbon.

The consequence of this finding is that the stereochemistry in Compounds 1, 3,4-11, and 13-16 are incorrectly represented at the asymmetric carbon and the correct representation to be one where the bond is inverted. For example, Compound 1 should be drawn as shown in 1a; 3 should be drawn as shown in 3a; and 4 should be drawn as shown in 4a; and so on.

To be clear, Compounds 1a, 3a, 4a-1a, and 13a-16a were originally made and tested following the General Schemes above. The studies conducted, as described in Examples 1-3 below and shown in FIGS. 1-4, utilized Compound 9a, not Compound 9.

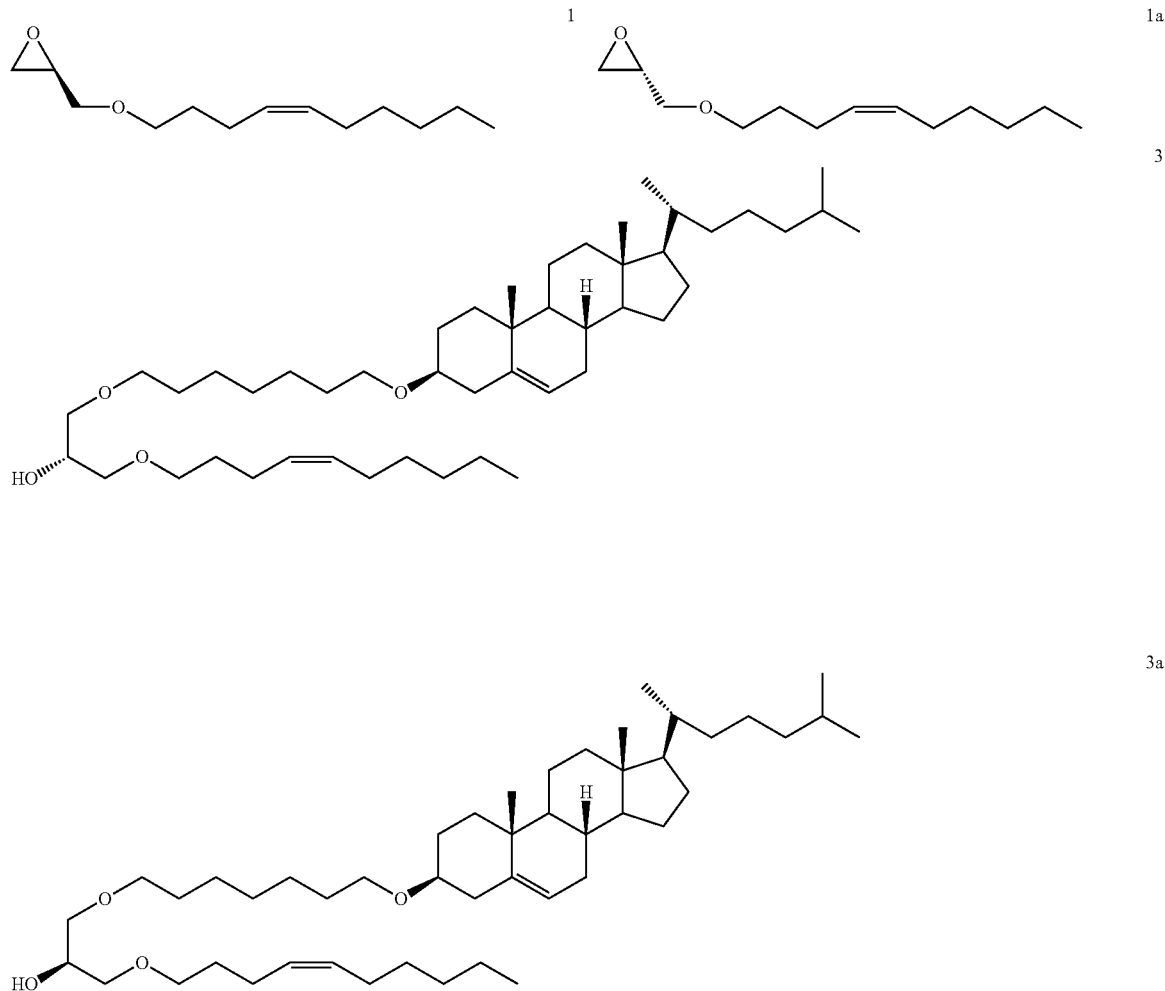

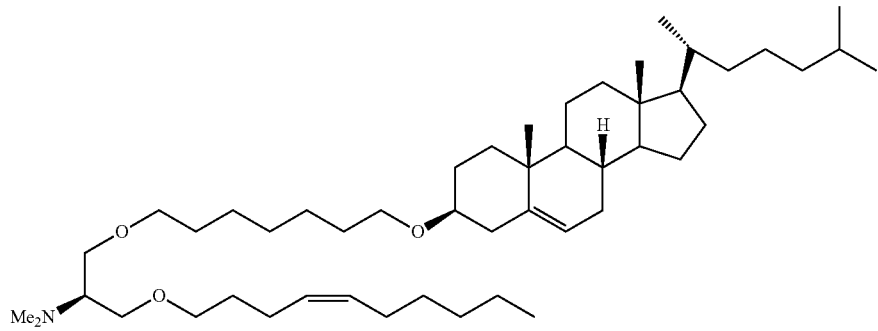
4
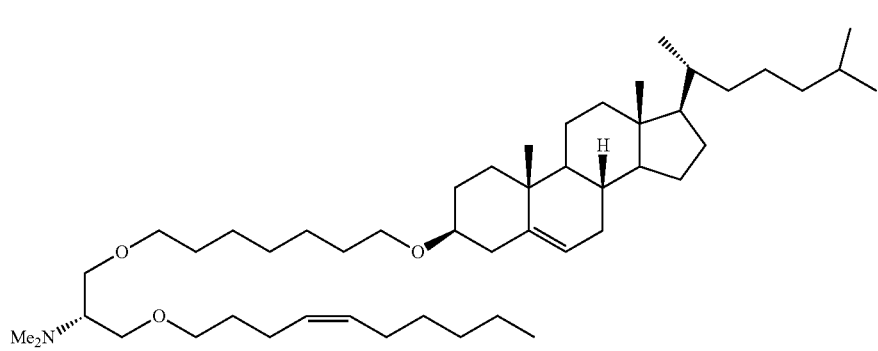
4a
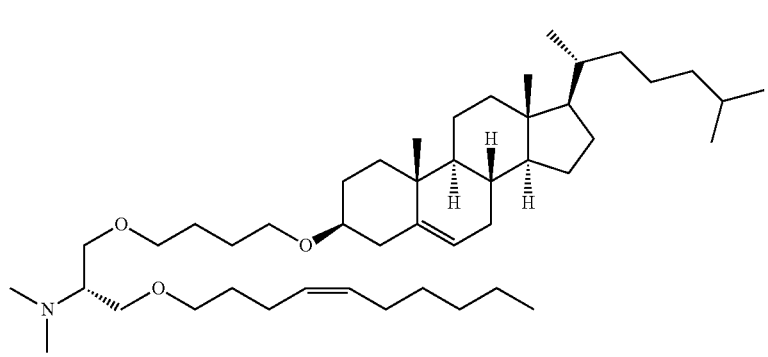
Compound 5a
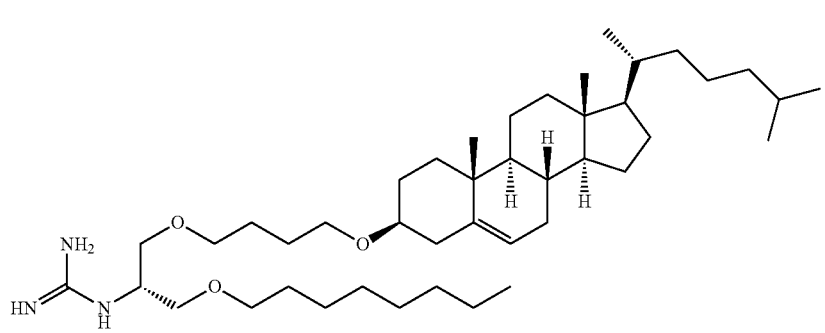
Compound 6a

-continued
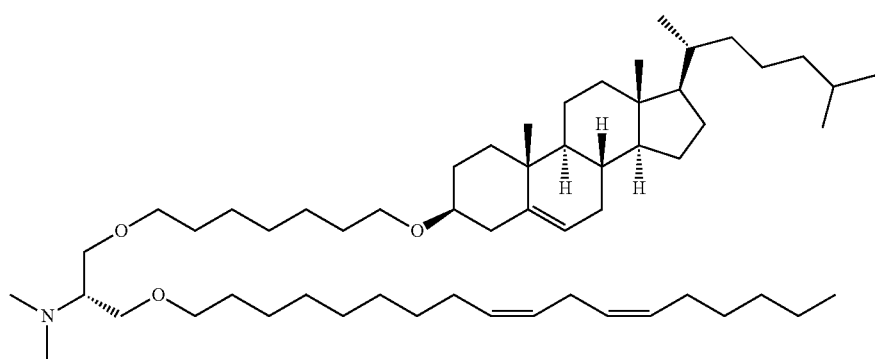
Compound 7a
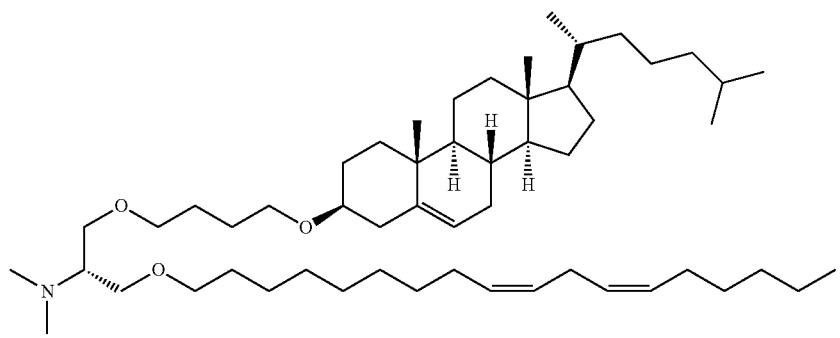
Compound 8a
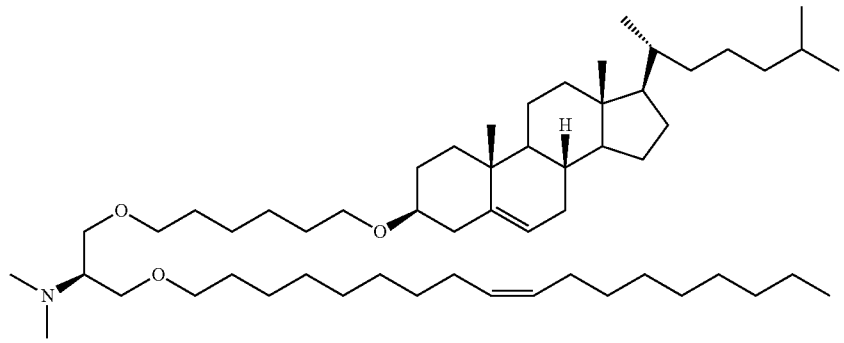
Compound 9a
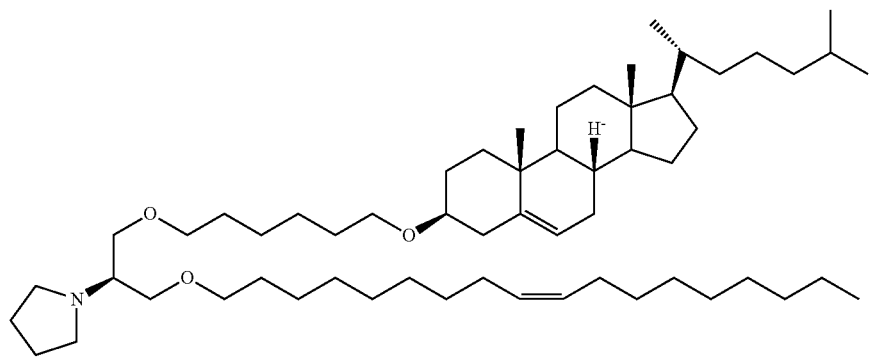
Compound 10a -continued
Compound 11a
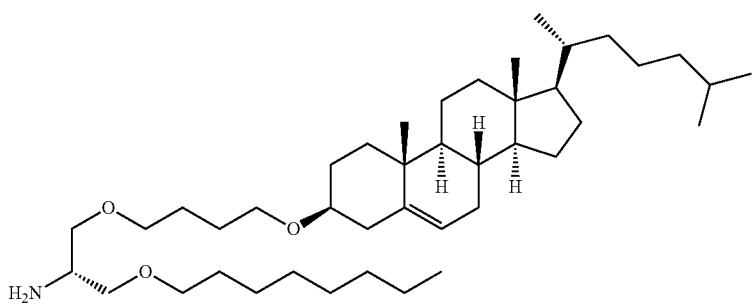
Compound 12
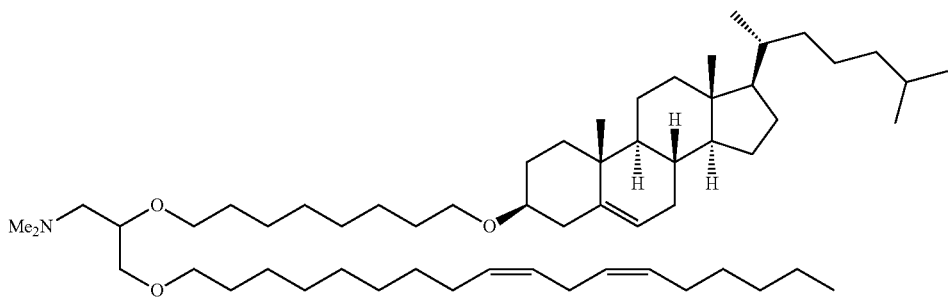
Compound 13a
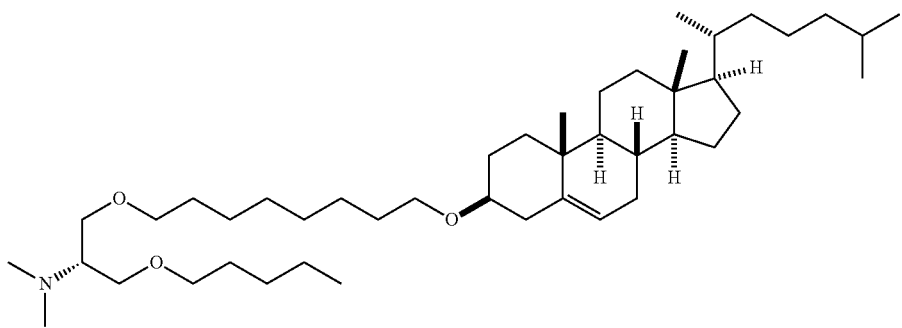
Compound 14a
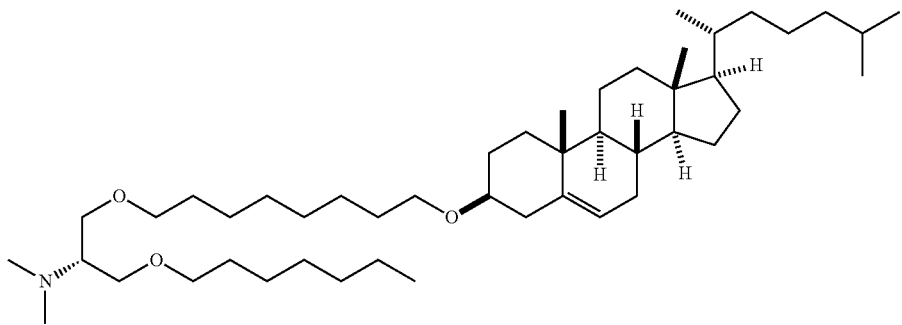
Compound 15a
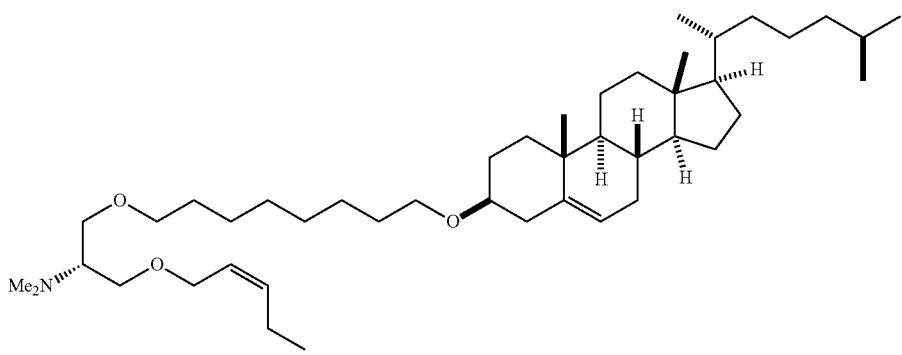

-continued

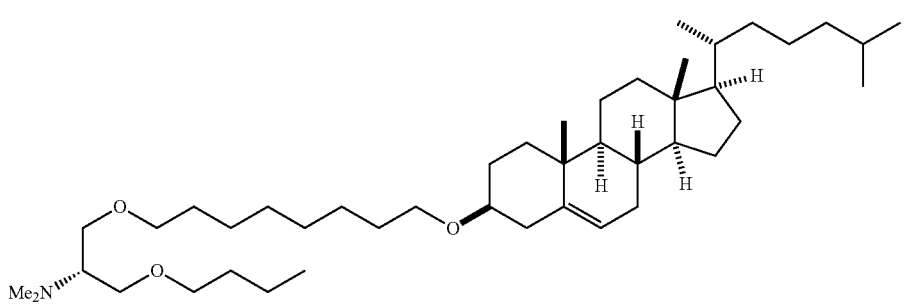
Compound 16a

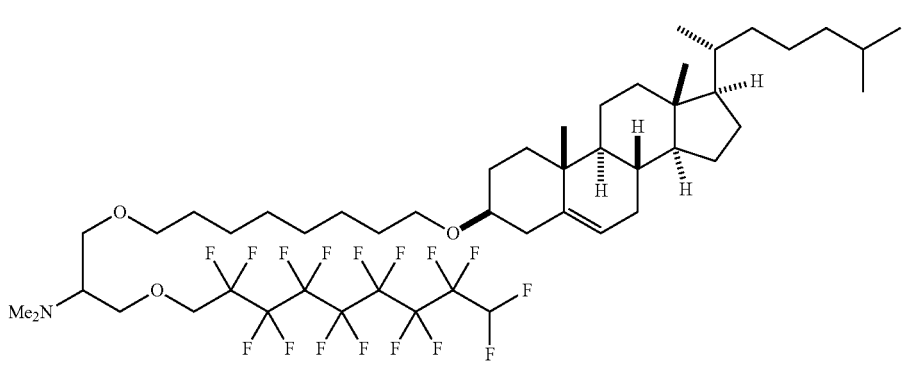
Compound 17

(2R)-1-{7-[(3β)-cholest-5-en-3-yloxy]heptyloxy}-3-[(4Z)-dec-4-en-1-yloxy]-N,N-dimethylpropan-2-amine (Compound 4a);
(2S )-1-{4-[(3β)-cholest-5-en-3-yloxy]butoxy}-3-[(4Z)-dec-4-en-1-yloxy]-N,N-dimethylpropan-2-amine (Compound 5a);
1-[(2S)-1-{4-[(3β)-cholest-5-en-3-yloxy]butoxy}-3-(octyloxy)propan-2-yl]guanidine (Compound 6a);
1-[(2S )-1-{7-[(3β)-cholest-5-en -3-yloxy]heptyloxy}-N,N-dimethyl-3-[(9Z, 12Z)octadeca-9,12-dien-1-yloxy]propan-2-amine (Compound 7a);
1-[(2S)-1-{4-[(3β)-cholest-5-en-3-yloxy]butoxy}-N,N-dimethyl-3-[(9Z, 12Z)-octadeca-9,12-dien-1-yloxy]propan-2-amine (Compound 8a);
(2R)-1-({6-[(3β))-cholest-5-en-3-yloxy]hexyl}oxy)-N,N,-dimethyl-3-[(9Z)-octadec-9-en-1-yloxy]propan-2-amine (Compound 9a);
(3β)-3-[6-{[(2R)-3-[(9Z)-octadec-9-en-1-yloxyl]-2-(pyrrolidin-1-yl)propyl]oxy}hexyl)oxy]cholest-5-ene (Compound 10a);
(2S)-1-{4-[(3β)-cholest-5-en-3-yloxy]butoxy}-3-(octyloxy)propan-2-amine (Compound 11a);
(2S)-1-({8-[(3β)cholest-5en-3-yloxy]octyl}oxy)-N,N-dimenthyl-3-(pentyloxy)propan-2-amine (Compound 13a);
(2S)-1-({8-[(3β)-cholest-5-en-3-yloxy]octyl}oxy)-3(heptyloxy)-N,N-dimethylpropan-2-amine (Compound 14a);
(2S)-1-({8-[(3β)-cholest-5-en-3-yloxy]octyl}oxy)-N,N-dimethyl-3-[(2Z)-pent-2-en-1-yloxy]propan-2-amine (Compound 15a); and
(2R)-1-butoxy-3-({8-[(3β)-cholest-5-en-3-yloxy]octyl}oxy)-N,N-dimethylpropan-2-amine (Compound 16a)

LNP COMPOSITIONS

LNP Process Description 1:

The Lipid Nano-Particles (LNP) are prepared by an impinging jet process. The particles are formed by mixing equal volumes of lipids dissolved in alcohol with siRNA dissolved in a citrate buffer. The lipid solution contains a novel cationic lipid of the instant invention, a helper lipid (cholesterol) and PEG (PEG-DMG) lipid at a concentration of 5-15 mg/mL with a target of 9-12 mg/mL in an alcohol (for example ethanol). The ratio of the lipids has a mole percent range of 25-98 for the cationic lipid with a target of 45-65, the helper lipid has a mole percent range from 0-75 with a target of 30-50 and the PEG lipid has a mole percent range from 1 -6 with a target of 2-5. The siRNA solution contains one or more siRNA sequences at a concentration range from 0.7 to 1 .0 mg/mL with a target of 0.8 -0.9 mg/mL in a sodium citrate: sodium chloride buffer pH 4. The two liquids are mixed in an impinging jet mixer instantly forming the LNP. The teeID has a range from 0.25 to 1.0 mm and a total flow rate from 10 -200 mL/min. The combination of flow rate and tubing ID has effect of controlling the particle size of the LNPs between 50 and 200 nm. The mixed LNPs are held from 30 minutes to 48 hrs prior to a dilution step. The dilution step comprises similar impinging jet mixing which instantly dilutes the LNP. This process uses tubing IDs ranging from 1 mm ID to 5 mm ID and a flow rate from 10 to 400 mL/min. The LNPs are concentrated and diafiltered via an ultrafiltration process where the alcohol is removed and the citrate buffer is exchanged for the final buffer solution such as phosphate buffered saline. The ultrafiltration process uses a tangential flow filtration format (TFF). This process uses a membrane nominal molecular weight cutoff range from 30-500 KD. The membrane format can be hollow fiber or flat sheet cassette. The TFF processes with the proper molecular weight cutoff retains the LNP in the retentate and the filtrate or permeate contains the alcohol; citrate buffer; final buffer wastes. The TFF process is a multiple step process with an initial concentration to a siRNA concentration of 1-3 mg/mL. Following concentration, the LNPs solution is diafiltered against the final buffer for 15-20 volumes to remove the alcohol and perform buffer exchange. The material is then concentrated an additional 1-3 fold. The final steps of the LNP process are to sterile filter the concentrated LNP solution and vial the product.

Analytical Procedure:

1) siRNA Concentration

The siRNA duplex concentrations are determined by Strong Anion-Exchange High-Performance Liquid Chromatography (SAX-HPLC) using Waters 2695 Alliance system (Water Corporation, Milford Mass.) with a 2996 PDA detector. The LNPs, otherwise referred to as RNAi Delivery Vehicles (RDVs), are treated with 0.5% Triton X-100 to free total siRNA and analyzed by SAX separation using a Dionex BioLC DNAPac PA 200 (4×250 mm) column with UV detection at 254 nm. Mobile phase is composed of A: 25 mM $NaClO_4$, 10 mM Tris, 20% EtOH, pH 7.0 and B: 250 mM $NaClO_4$, 10 mM Tris, 20% EtOH, pH 7.0 with liner gradient from 0-15 min in and flow rate of 1 ml/min. The siRNA amount is determined by comparing to the siRNA standard curve.

2) Encapsulation Rate

Fluorescence reagent SYBR Gold is employed for RNA quantitation to monitor the encapsulation rate of RDVs. RDVs with or without Triton X-100 are used to determine the free siRNA and total siRNA amount. The assay is performed using a SpectraMax M5e microplate spectrophotometer from Molecular Devices (Sunnyvale, Calif.). Samples are excited at 485 nm and fluorescence emission was measured at 530 nm. The siRNA amount is determined by comparing to the siRNA standard curve.

Encapsulation rate=(1-free siRNA/total siRNA)× 100%

3) Particle Size and Polydispersity

RDVs containing 1 μg siRNA are diluted to a final volume of 3 ml with 1×PBS. The particle size and polydispersity of the samples is measured by a dynamic light scattering method using ZetaPALS instrument (Brookhaven Instruments Corporation, Holtsville, N.Y.). The scattered intensity is measured with He—Ne laser at 25° C. with a scattering angle of 90°.

4) Zeta Potential Analysis

RDVs containing 1 μg siRNA are diluted to a final volume of 2 ml with 1 mM Tris buffer (pH 7.4). Electrophoretic mobility of samples is determined using ZetaPALS instrument (Brookhaven Instruments Corporation, Holtsville, N.Y.) with electrode and He—Ne laser as a light source. The Smoluchowski limit is assumed in the calculation of zeta potentials.

5) Lipid Analysis

Individual lipid concentrations are determined by Reverse Phase High-Performance Liquid Chromatography (RP-HPLC) using Waters 2695 Alliance system (Water Corporation, Milford Mass.) with a Corona charged aerosol detector (CAD) (ESA Biosciences, Inc. Chelmsford, Mass.). Individual lipids in RDVs are analyzed using an Agilent Zorbax SB-C18 (50×4.6 mm, 1.8 μm particle size) column with CAD at 60° C. The mobile phase is composed of A: 0.1% TFA in $H_2O$ and B: 0.1% TFA in IPA. The gradient is 75% mobile phase A and 25% mobile phase B from time 0 to 0.10 min; 25% mobile phase A and 75% mobile phase B from 0.10 to 1.10 min; 25% mobile phase A and 75% mobile phase B from 1.10 to 5.60 min; 3% mobile phase A and 95% mobile phase B from 5.60 to 8.01 min; and 75% mobile phase A and 25% mobile phase B from 8.01 to 13 min with flow rate of 1 ml/min. The individual lipid concentration is determined by comparing to the standard curve with all the lipid components in the RDVs with a quadratic curve fit. The molar percentage of each lipid is calculated based on its molecular weight.

Utilizing the above described LNP process, specific LNPs with the following ratios and siRNAs were identified:

Nominal Composition:

```
Cationic Lipid/Cholesterol/PEG-DMG 60/38/2.
Luc siRNA
                                     (SEQ. ID. NO.: 1)
5'-iB-AUAAGGCUAUGAAGAGAUAUU-iB 3'

(SEQ. ID. NO.: 2)
3'-UUUAUUCCGAUACUUCUCUAU-5'

AUGC - Ribose iB-Inverted deoxy abasic

UC - 2' Fluoro

AGT - 2' Deoxy

AGU - 2' OCH₃

Cationic Lipid/Cholesterol/PEG-DMG 60/38/2
ApoB siRNA
                                     (SEQ ID NO.: 3)
5'-iB-CUUUAACAAUUCCUGAAAUTT-iB (SEQ ID NO.: 4)
3'-UUGAAAUUGUUAAGGACUUUA-5'

AUGC - Ribose iB - Inverted deoxy abasic

UC - 2' Fluoro

AGT - 2' Deoxy

AGU - 2' OCH₃
```

LNP Process Description 2:

The Lipid Nano-Particles (LNP) are prepared by an impinging jet process. The particles are formed by mixing lipids dissolved in alcohol with siRNA dissolved in a citrate buffer. The mixing ratio of lipids to siRNA are targeted at 45-55% lipid and 65-45% siRNA. The lipid solution contains a novel cationic lipid of the instant invention, a helper lipid (cholesterol), PEG (e.g. PEG-C-DMA, PEG-DMG) lipid, and DSPC at a concentration of 5-15 mg/mL with a target of 9-12 mg/mL in an alcohol (for example ethanol). The ratio of the lipids has a mole percent range of 25-98 for the cationic lipid with a target of 35-65, the helper lipid has a mole percent range from 0-75 with a target of 30-50, the PEG lipid has a mole percent range from 1-15 with a target of 1-6, and the DSPC has a mole precent range of 0-15 with a target of 0-12. The siRNA solution contains one or more siRNA sequences at a concentration range from 0.3 to 1 .0 mg/mL with a target of 0.3 -0.9 mg/mL in a sodium-citrate buffered salt solution with pH in the range of 3.5-5. The two liquids are heated to a temperature in the range of 15-40° C., targeting 30-40° C., and then mixed in an impinging jet mixer instantly forming the LNP. The teeID has a range from 0.25 to 1.0 mm and a total flow rate from 10 -600 mL/min. The combination of flow rate and tubing ID has effect of controlling the particle size of the LNPs between 30 and 200 nm. The solution is then mixed with a buffered solution at a higher pH with a mixing ratio in the range of 1:1 to 1:3 vol:vol but targeting 1:2 vol:vol. This buffered solution is at a temperature in the range of 15-40° C., targeting 30-40° C. The mixed LNPs are held from 30 minutes to 2 hrs prior to an anion exchange filtration step. The temperature during incubating is in the range of 15-40° C., targeting 30-40° C. After incubating the solution is filtered through a 0.8 um filter containing an anion exchange separation step. This process uses tubing IDs ranging from 1 mm ID to 5 mm ID and a flow rate from 10 to 2000 mL/min. The LNPs are concentrated and diafiltered via an ultrafiltration process where the alcohol is removed and the citrate buffer is exchanged for the final buffer solution such as phosphate buffered saline. The ultrafiltration process uses a tangential flow filtration format (TFF). This process uses a membrane nominal molecular weight cutoff range from 30-500 KD. The membrane format can be hollow fiber or flat sheet cassette. The TFF processes with the proper molecular weight cutoff retains the LNP in the retentate and the filtrate or permeate contains the alcohol; citrate buffer; final buffer wastes. The TFF process is a multiple step process with an initial concentration to a siRNA concentration of 1-3 mg/mL. Following concentration, the LNPs solution is diafiltered against the final buffer for 10-20 volumes to remove the alcohol and perform buffer exchange. The material is then concentrated an additional 1-3 fold. The final steps of the LNP process are to sterile filter the concentrated LNP solution and vial the product.

EXAMPLE 1

Mouse In Vivo Evaluation of Efficacy and Toxicity

LNPs utilizing Compound 9 or 12, in the nominal compositions described immediately above, were evaluated for in vivo efficacy and induction of inflammatory cytokines in a luciferase mouse model. The siRNA targets the mRNA transcript for the firefly (*Photinus pyralis*) luciferase gene (Accession # M15077). The primary sequence and chemical modification pattern of the luciferase siRNA is displayed above. The in vivo luciferase model employs a transgenic mouse in which the firefly luciferase coding sequence is present in all cells. ROSA26-LoxP-Stop-LoxP-Luc (LSL-Luc) transgenic mice licensed from the Dana Farber Cancer Institute are induced to express the Luciferase gene by first removing the LSL sequence with a recombinant Ad-Cre virus (Vector Biolabs). Due to the organo-tropic nature of the virus, expression is limited to the liver when delivered via tail vein injection. Luciferase expression levels in liver are quantitated by measuring light output, using an IVIS imager (Xenogen) following administration of the luciferin substrate (Caliper Life Sciences). Pre-dose luminescence levels are measured prior to administration of the RDVs. Luciferin in PBS (15 mg/mL) is intraperitoneally (IP) injected in a volume of 150 uL. After a four minute incubation period mice are anesthetized with isoflurane and placed in the IVIS. imager. The RDVs (containing siRNA) in PBS vehicle were tail vein injected in a volume of 0.2 mL. Final dose levels ranged from 0.3 to 3 mg/kg siRNA. PBS vehicle alone was dosed as a control. Three hours post dose, mice were bled retro-orbitally to obtain plasma for cytokine analysis. Mice were imaged 48 hours post dose using the method described above. Changes in luciferin light output directly correlate with luciferase mRNA levels and represent an indirect measure of luciferase siRNA activity. In vivo efficacy results are expressed as % inhibition of luminescence relative to pre-dose luminescence levels. Plasma cytokine levels were determined using the SearchLight multiplexed cytokine chemoluminescent array (Pierce/Thermo). Systemic administration of the luciferase siRNA RDVs decreased luciferase expression in a dose dependant manner. Greater efficacy was observed in mice dosed with compounds 9 containing RDVs than with the RDV containing the octyl-CLinDMA cationic lipid. Compound 12, (Table 1 and FIG. 2). Compound 9 and 12 RDVs significantly increased mouse plasma levels of the cytokines IL-6 and mKC relative to the PBS control. However, average cytokine induction was lower in the animals dosed with the Compound 9 RDV, relative to the Compound 12 RDV.(FIG. 1).

TABLE 1

Mouse In Vivo efficacy data. Average % Inhibition of Bioluminescence by LNPs prepared from compounds 9 and 12

| Compound 9 | | | Compound 12 | | |
| --- | --- | --- | --- | --- | --- |
| 0.1 mg Kg$^{-1}$ | 0.3 mg Kg$^{-1}$ | 1.0 mg Kg$^{-1}$ | 0.1 mg Kg$^{-1}$ | 0.3 mg Kg$^{-1}$ | 1.0 mg Kg$^{-1}$ |
| 80 | 89 | 91 | 54 | 74 | 88 |

EXAMPLE 2

Rat In Vivo Evaluation of Efficacy and Toxicity

Figure 3:
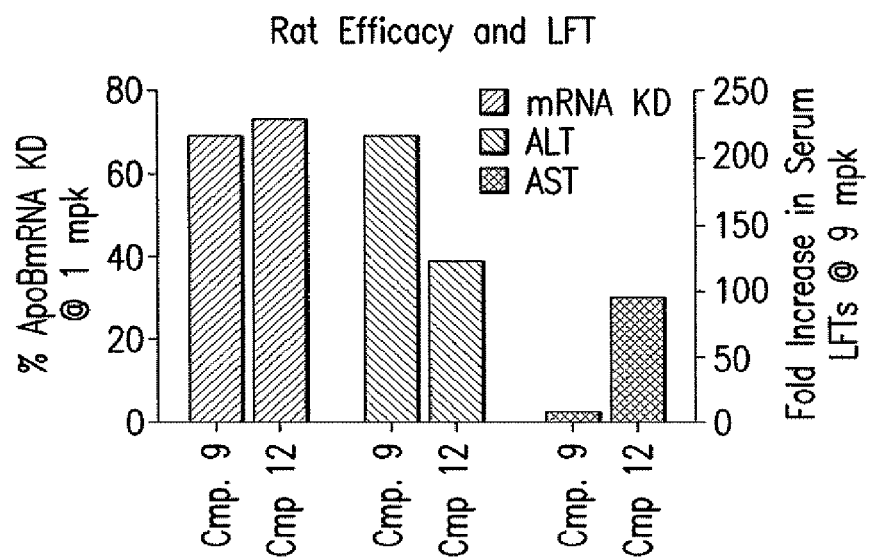
FIG. 3: Rat data comparing Compound 12 with Compound 9.

LNPs utilizing Compounds 9 or 12 in the nominal compositions described above, were evaluated for in vivo efficacy and increases in alanine amino transferase and aspartate amino transferase in Sprague-Dawley (Crl:CD(SD) female rats (Charles River Labs). The siRNA targets the mRNA transcript for the ApoB gene (Accession # NM 019287). The primary sequence and chemical modification pattern of the ApoB siRNA is displayed above. The-RDVs (containing siRNA) in PBS vehicle were tail vein injected in a volume of 1 to 1.5 mL. Infusion rate is approximately 3 ml/min. Five rats were used in each dosing group. After LNP administration, rats are placed in cages with normal diet and water present. Six hours post dose, food is removed from the cages. Animal necropsy is performed 24 hours after LNP dosing. Rats are anesthetized under isoflurane for 5 minutes, then maintained under anesthesia by placing them in nose cones continuing the delivery of isoflurane until ex-sanguination is completed. Blood is collected from the vena cava using a 23 guage butterfly venipuncture set and aliquoted to serum separator vacutainers for serum chemistry analysis. Punches of the excised caudate liver lobe are taken and placed in RNA Later (Ambion) for mRNA analysis. Preserved liver tissue was homogenized and total RNA isolated using a Qiagen bead mill and the Qiagen miRNA-Easy RNA isolation kit following the manufacturer's instructions. Liver ApoB mRNA levels were determined by quantitative RT-PCR. Message was amplified from purified RNA utilizing a rat ApoB commercial probe set (Applied Biosystems Cat # RN01499054_m1). The PCR reaction was performed on an ABI 7500 instrument with a 96-well Fast Block. The ApoB mRNA level is normalized to the housekeeping PPIB (NM 011149) mRNA. PPIB mRNA levels were determined by RT-PCR using a commercial probe set (Applied Biosytems Cat. No. Mm00478295_m1). Results are expressed as a ratio of ApoB mRNA/PPIB mRNA. All mRNA data is expressed relative to the PBS control dose. Serum ALT and AST analysis were performed on the Siemens Advia 1800 Clinical Chemistry Analyzer utilizing the Siemens alanine aminotransferase (Cat# 03039631) and aspartate aminotransferase (Cat# 03039631) reagents. The RDVs employing both Compounds 9 and 12 displayed similar levels of ApoB mRNA knock down at the 1 mpk dose (FIG. 3). An increase in LFTs were observed for both RDVs, relative to PBS control dosed rats (FIG. 3). While ALT levels increased to a greater extent in rats dosed with the Compound 9 RDV, AST levels increased more strongly with the Compound 12 RDV (FIG. 3).

EXAMPLE 3

Rhesus Monkey In Vivo Evaluation of Efficacy and Toxicity

Figure 4:
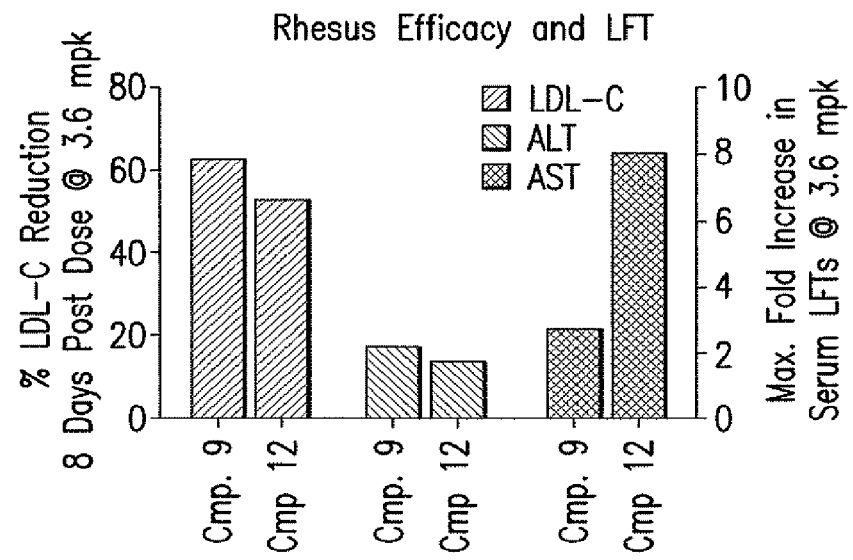
FIG. 4: Monkey data comparing Compound 12 with Compound 9.

LNPs utilizing Compounds 9 or 12 in the nominal compositions described above, were evaluated for in vivo efficacy and increases in alanine amino transferases (ALT) and aspartate amino transferase (AST) in male or female *Macaca mulatta* (rhesus) monkeys. The siRNA targets the mRNA transcript for the ApoB gene (Accession # XM 001097404). The primary sequence and chemical modification pattern of the ApoB siRNA is displayed above. The RDVs (containing siRNA) in PBS vehicle were administered by intravenous injection in the saphenous vein at an injection rate of 20 mL/minute to a dose level of 3.6 mg/kilogram siRNA. The injection volumes were from 1.9 to 2.1 mL/kilogram and monkeys ranged in weight from 2.5 to 4.5 kilograms. Each RDV or PBS control was administered to two monkeys. At multiple days post dose, 1 mL blood samples were drawn from the femoral artery for serum chemistry analysis. Monkeys were fasted overnight prior to blood draws. Serum ALT and AST analysis were performed on the Siemens Advia 1800 Clinical Chemistry Analyzer utilizing the Siemens alanine aminotransferase (Cat# 03039631) and aspartate aminotransferase (Cat# 03039631) reagents. As a measure of efficacy, LDL-C was monitored as a downstream surrogate marker of ApoB mRNA reduction. At eight days post systemic administration, of RDVs containing Compounds 9 or 12, reduced serum levels of LDL-C to less than 50% of pre-dose levels (FIG. 4). The RDV containing Compound 9 reduced LDL-C levels to a greater extent than the RDV containing Compound 12 (ave.: −63% vs. −53%). ALT and AST were elevated relative to predose values in monkeys treated with both Compounds 9 and 12 RDVs (FIG. 4). Elevation of ALT was approximately equivalent for both RDVs, but AST was elevated to a markedly higher level in the RDV containing Compound 12.

What is claimed is:

1. A lipid nanoparticle comprising a cationic lipid of Formula A:

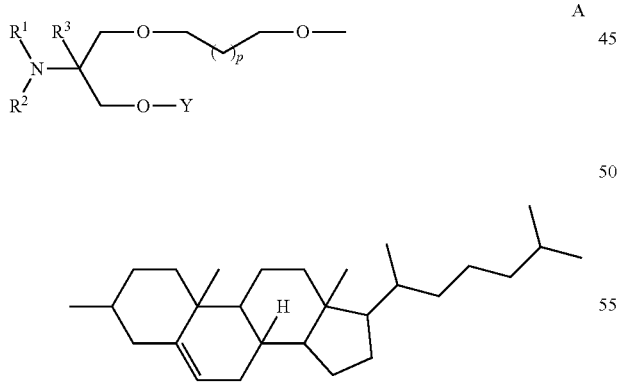

wherein:

p is 1 to 8;

$R^1$ and $R^2$ are independently selected from H, $(C_1-C_{10})$ alkyl, heterocyclyl, and a polyamine, wherein said heterocyclyl and polyamine are optionally substituted with one to three substituents selected from $R^4$, or $R^1$ and $R^2$ can be taken together with the nitrogen to which they are attached to form a monocyclic heterocycle with 4-7 members optionally containing, in addition to the nitrogen, one or two additional heteroatoms selected from N, O and S, said monocyclic heterocycle optionally substituted with one to three substituents selected from $R^4$;

$R^3$ is selected from H and $(C_1-C_6)$alkyl, said alkyl optionally substituted with one to three substituents selected from $R^4$;

$R^4$ is independently selected from halogen, $OR^5$, $SR^5$, CN, $CO_2R^5$ and $CON(R^5)_2$;

$R^5$ is independently selected from H, $(C_1-C_{10})$alkyl and aryl; and

Y is a $(C_4-C_{22})$alkyl, $(C_4-C_{22})$perfluoroalkyl, or a $(C_4-C_{22})$alkenyl;

or any pharmaceutically acceptable salt or stereoisomer thereof.

2. The lipid nanoparticle of claim 1, wherein:

p is 1 to 8;

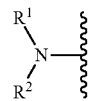

is selected from:

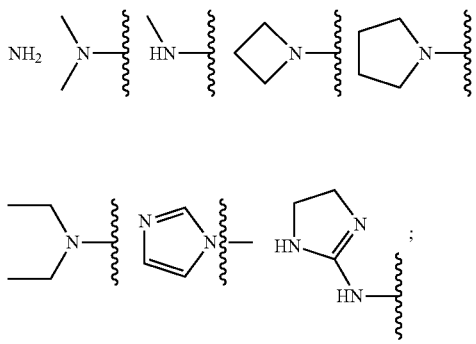

R³ is H; and
Y is a (C₄-C₂₂)alkyl, (C₄-C₂₂)perfluoroalkyl, or a (C₄-C₂₂)alkenyl;
or any pharmaceutically acceptable salt or stereoisomer thereof.

3. The lipid nanoparticle of claim 1, wherein the cationic lipid is selected from:
(2S)-1-{7-[(3β)-cholest-5-en-3-yloxy]heptyloxy}-3-[(4Z)-dec-4-en-1-yloxy]-N,N-dimethylpropan-2-amine (Compound 4);
(2R)-1-{4-[(3β)-cholest-5-en-3-yloxy]butoxy}-3-[(4Z)-dec-4-en-1-yloxy]-N,N-dimethylpropan-2-amine (Compound 5);
(2R)-1-{7-[(3β)-cholest-5-en-3-yloxy]heptyloxy}-N,N-dimethyl-3-[(9Z,12Z)-octadeca-9,12-dien-1-yloxy]propan-2-amine (Compound 7);
(2R)-1-{4-[(3β)-cholest-5-en-3-yloxy]butoxy}-N,N-dimethyl-3-[(9Z,12Z)-octadeca-9,12-dien-1-yloxy]propan-2-amine (Compound 8);
(2 S)-1 -({6-[(3β)-cholest-5 -en-3 -yloxy]hexyl}oxy)-N,N-dimethyl-3-[(9Z)-octadec-9-en-1-yloxy]propan-2-amine (Compound 9);
(3β)-3-[6-{[(2S)-3-[(9Z)-octadec-9-en-1-yloxyl]-2-(pyrrolidin-1-yl)propyl]oxy}hexyloxy]cholest-5-ene (Compound 10);
(2R)-1-{4-[(3β)-cholest-5-en-3-yloxy]butoxy}-3-(octyloxy)propan-2-amine (Compound 11);
(2R)-1-({8-[(3β)-cholest-5-en-3-yloxy]octyl}oxy)-N,N-dimethyl-3-(pentyloxy)propan-2-amine (Compound 13);
(2R)-1-({8-[(3β)-cholest-5-en-3-yloxy]octyl}oxy)-3-(heptyloxy)-N,N-dimethylpropan-2-amine (Compound 14);
(2R)-1-({8-[(3β)-cholest-5-en-3-yloxy]octyl}oxy)-N,N-dimethyl-3-[(2Z)-pent-2-en-1-yloxy]propan-2-amine (Compound 15);
(2S)-1-butoxy-3-({8-[(3β)-cholest-5-en-3-yloxy]octyl}oxy)-N,N-dimethylpropan-2-amine (Compound 16);
(2S)-1-({8-[(3β)-cholest-5-en-3-yloxy]octyl}oxy)-3-[2,2,3,3,4,4,5,5,6,6,7,7,8,8,9,9-hexadecafluorononyl]oxy-N,N-dimethylpropan-2-amine(Compound 17);
2-amino-3-({9-[(3β,8ξ,9ξ,14ξ,17ξ,20ξ)-cholest-5-en-3-yloxy]nonyl}oxy)-2-{[(9Z,12Z) -octadeca-9,12-dien-1-yloxy]methyl}propan-1-ol (Compound 19); and;
2-amino-3-({6-[(3β,8ξ,14ξ,17ξ,20ξ)-cholest-5-en-3-yloxy]hexyl}oxy)-2-{[(9Z) -octadec-9-en-1-yloxy]methyl}propan-1-ol (Compound 20);
or any pharmaceutically acceptable salt or stereoisomer thereof.

4. The lipid nanoparticle of claim 1, wherein the cationic lipid is selected from:
(2R)-1-{7-[(3β)-cholest-5-en-3-yloxy]heptyloxy}-3-[(4Z)-dec-4-en-1-yloxy]-N,N-dimethylpropan-2-amine (Compound 4a);
(2S)-1-{4-[(3β)-cholest-5-en-3-yloxy]butoxy}-3-[(4Z)-dec-4-en-1-yloxy]-N,N-dimethylpropan-2-amine (Compound 5a);
(2S)-1-{7-[(3β)-cholest-5-en-3-yloxy]heptyloxy}-N,N-dimethyl-3-[(9Z,12Z)-octadeca-9,12-dien-1-yloxy]propan-2-amine (Compound 7a);
(2S)-1-{4-[(3β)-cholest-5-en-3-yloxy]butoxy}-N,N-dimethyl-3-[(9Z,12Z)-octadeca-9,12-dien-1-yloxy]propan-2-amine (Compound 8a);
(2R)-1-({6-[(3β)-cholest-5-en-3-yloxy]hexyl}oxy)-N,N-dimethyl-3-[(9Z)-octadec-9-en-1-yloxy]propan-2-amine (Compound 9a);
(3β)-3-[6-{[(2R)-3-[(9Z)-octadec-9-en-1-yloxyl]-2-(pyrrolidin-1-yl)propyl]oxy}hexyloxy]cholest-5-ene (Compound 10a);
(2S)-1-{4-[(3β)-cholest-5-en-3-yloxy]butoxy}-3-(octyloxy)propan-2-amine (Compound 11a);
(2S)-1-({8-[(3β)-cholest-5-en-3-yloxy]octyl}oxy)-N,N-dimethyl-3-(pentyloxy)propan-2-amine(Compound 13a);
(2S)-1-({8-[(3β)-cholest-5-en-3-yloxy]octyl}oxy)-3-(heptyloxy)-N,N-dimethylpropan-2-amine(Compound 14a);
(2R)-1-({8-[(3β)-cholest-5-en-3-yloxy]octyl}oxy)-N,N-dimethyl-3-[(2Z)-pent-2-en-1-yloxy]propan-2-amine (Compound 15a); and
(2R)-1-butoxy-3-({8-[(3β)-cholest-5-en-3-yloxy]octyl}oxy)-N,N-dimethylpropan-2-amine(Compound 16a).

5. The lipid nanoparticle of claim 1, wherein the cationic lipid is:
(2S)-1-({6-[(3β)-cholest-5-en-3-yloxy]hexyl}oxy)-N,N-dimethyl-3-[(9Z)-octadec-9-en-1-yloxy]propan-2-amine(Compound 9); or (2R)-1-({6-[(3β)-cholest-5-en-3-yloxy]hexyl}oxy)-N,N-dimethyl-3-[(9Z)-octadec-9-en-1-yloxy]propan-2-amine (Compound 9a)
or any pharmaceutically acceptable salt or stereoisomer thereof.

6. The lipid nanoparticle of claim 1, wherein the nanoparticle further comprises an oligonucleotide.

7. The lipid nanoparticle of claim 6, wherein the oligonucleotide is siRNA or miRNA.

8. The lipid nanoparticle of claim 7, wherein the oligonucleotide is siRNA.

9. A lipid nanoparticle comprising a cationic lipid of Formula A:

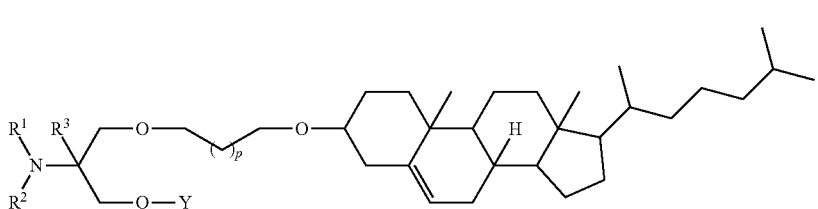

wherein:

p is 1 to 8;

is selected from:

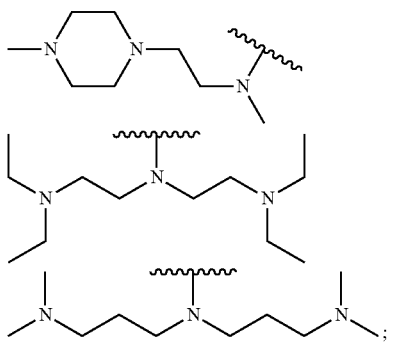

n is 1 to 10;
R³ is H; and
Y is a (C₄-C₂₂)alkyl, (C₄-C₂₂)perfluoroalkyl, or a (C₄-C₂₂)alkenyl;

or any pharmaceutically acceptable salt or stereoisomer thereof.

10. The lipid nanoparticle of claim 9, wherein the nanoparticle further comprises an oligonucleotide.

11. The lipid nanoparticle of claim 10, wherein the oligonucleotide is siRNA or miRNA.

12. The lipid nanoparticle of claim 11, wherein the oligonucleotide is siRNA.

13. A lipid nanoparticle comprising a cationic lipid of Formula A:

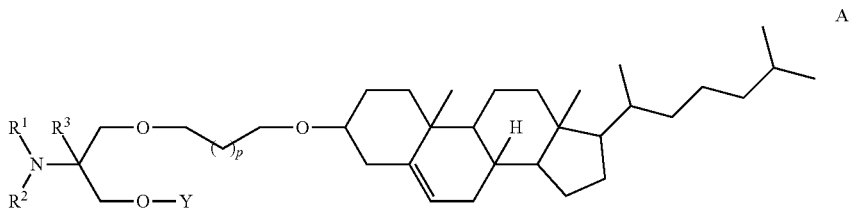

wherein:

p is 1 to 8;

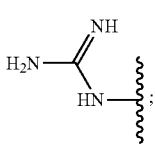

is

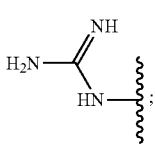

R³ is H; and

Y is a (C₄-C₂₂)alkyl, (C₄-C₂₂)perfluoroalkyl, or a (C₄-C₂₂)alkenyl;

or any pharmaceutically acceptable salt or stereoisomer thereof.

14. The lipid nanoparticle of claim 13, wherein the cationic lipid is:

1-[(2R)-1-{4-[(3β)-cholest-5-en-3-yloxy]butoxy}-3-(octyloxy)propan-2-yl]guanidine (Compound 6); or 1-[(2S)-1-{4-[(3β)-cholest-5-en-3-yloxy]butoxy}-3-(octyloxy)propan-2-yl]guanidine.

15. The lipid nanoparticle of claim 13, wherein the nanoparticle further comprises an oligonucleotide.

16. The lipid nanoparticle of claim 15, wherein the oligonucleotide is siRNA or miRNA.

17. The lipid nanoparticle of claim 16, wherein the oligonucleotide is siRNA.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Enzymatic Nucleic Acid
<221> NAME/KEY: misc_feature
<222> LOCATION: (1)...(1)
<223> OTHER INFORMATION: 2'-deoxy
<221> NAME/KEY: misc_feature
<222> LOCATION: (2)...(2)
<223> OTHER INFORMATION: 2'-fluoro
<221> NAME/KEY: misc_feature
<222> LOCATION: (3)...(6)
<223> OTHER INFORMATION: 2'-deoxy
<221> NAME/KEY: misc_feature
<222> LOCATION: (7)...(8)
<223> OTHER INFORMATION: 2'-fluoro
<221> NAME/KEY: misc_feature
<222> LOCATION: (9)...(9)
<223> OTHER INFORMATION: 2'-deoxy
<221> NAME/KEY: misc_feature
<222> LOCATION: (10)...(10)
<223> OTHER INFORMATION: 2'-fluoro
<221> NAME/KEY: misc_feature
<222> LOCATION: (11)...(17)
<223> OTHER INFORMATION: 2'-deoxy
<221> NAME/KEY: misc_feature
<222> LOCATION: (18)...(18)
<223> OTHER INFORMATION: 2'-fluoro
<221> NAME/KEY: misc_feature
<222> LOCATION: (19)...(21)
<223> OTHER INFORMATION: 2'-deoxy

<400> SEQUENCE: 1
auaaggcuau gaagagauat t                                              21
```

```
<210> SEQ ID NO 2
<211> LENGTH: 21
<212> TYPE: RNA
<213> ORGANISM: Artificial Sequence
<220> FEATURE:
<223> OTHER INFORMATION: Enzymatic Nucleic Acid
<221> NAME/KEY: misc_feature
<222> LOCATION: (1)...(3)
<223> OTHER INFORMATION: ribose
<221> NAME/KEY: misc_feature
<222> LOCATION: (4)...(9)
<223> OTHER INFORMATION: 2'-fluoro
<221> NAME/KEY: misc_feature
<222> LOCATION: (10)...(10)
<223> OTHER INFORMATION: 2'-o-methyl
<221> NAME/KEY: misc_feature
<222> LOCATION: (11)...(11)
<223> OTHER INFORMATION: 2'-fluoro
<221> NAME/KEY: misc_feature
<222> LOCATION: (12)...(13)
<223> OTHER INFORMATION: 2'-o-methyl
<221> NAME/KEY: misc_feature
<222> LOCATION: (14)...(17)
<223> OTHER INFORMATION: 2'-fluoro
<221> NAME/KEY: misc_feature
<222> LOCATION: (18)...(18)
<223> OTHER INFORMATION: 2'-o-methyl
<221> NAME/KEY: misc_feature
<222> LOCATION: (19)...(19)
<223> OTHER INFORMATION: 2'-fluoro
<221> NAME/KEY: misc_feature
<222> LOCATION: (20)...(21)
<223> OTHER INFORMATION: 2'-o-methyl

<400> SEQUENCE: 2
uuuauuccga uacuucucua u                                       21

<210> SEQ ID NO 3
<211> LENGTH: 21
<212> TYPE: DNA
<213> ORGANISM: Artificial Sequence
<220> FEATURE:
<223> OTHER INFORMATION: Enzymatic Nucleic Acid
<221> NAME/KEY: misc_feature
<222> LOCATION: (1)...(4)
<223> OTHER INFORMATION: 2'-fluoro
<221> NAME/KEY: misc_feature
<222> LOCATION: (5)...(6)
<223> OTHER INFORMATION: 2'-deoxy
<221> NAME/KEY: misc_feature
<222> LOCATION: (7)...(7)
<223> OTHER INFORMATION: 2'-fluoro
<221> NAME/KEY: misc_feature
<222> LOCATION: (8)...(9)
<223> OTHER INFORMATION: 2'-deoxy
<221> NAME/KEY: misc_feature
<222> LOCATION: (10)...(14)
<223> OTHER INFORMATION: 2'-fluoro
<221> NAME/KEY: misc_feature
<222> LOCATION: (15)...(18)
<223> OTHER INFORMATION: 2'-deoxy
<221> NAME/KEY: misc_feature
```

```
<222> LOCATION: (19)...(19)
<223> OTHER INFORMATION: 2'-fluoro
<221> NAME/KEY: misc_feature
<222> LOCATION: (20)...(21)
<223> OTHER INFORMATION: 2'-deoxy

<400> SEQUENCE: 3
cuuuaacaau uccugaaaut t                                          21

<210> SEQ ID NO 4
<211> LENGTH: 21
<212> TYPE: RNA
<213> ORGANISM: Artificial Sequence
<220> FEATURE:
<223> OTHER INFORMATION: Enzymatic Nucleic Acid
<221> NAME/KEY: misc_feature
<222> LOCATION: (1)...(6)
<223> OTHER INFORMATION: 2'-O-methyl
<221> NAME/KEY: misc_feature
<222> LOCATION: (7)...(8)
<223> OTHER INFORMATION: 2'-fluoro
<221> NAME/KEY: misc_feature
<222> LOCATION: (9)...(9)
<223> OTHER INFORMATION: 2'-O-methyl
<221> NAME/KEY: misc_feature
<222> LOCATION: (10)...(11)
<223> OTHER INFORMATION: 2'-fluoro
<221> NAME/KEY: misc_feature
<222> LOCATION: (12)...(16)
<223> OTHER INFORMATION: 2'-O-methyl
<221> NAME/KEY: misc_feature
<222> LOCATION: (17)...(18)
<223> OTHER INFORMATION: 2'-fluoro
<221> NAME/KEY: misc_feature
<222> LOCATION: (19)...(21)
<223> OTHER INFORMATION: ribose

<400> SEQUENCE: 4
uugaaauugu uaaggacuuu a                                          21
```